US010441769B2

(12) United States Patent
Hor et al.

(10) Patent No.: US 10,441,769 B2
(45) Date of Patent: Oct. 15, 2019

(54) TARGETED DELIVERY OF ACTIVE AGENTS USING THERMALLY STIMULATED LARGE INCREASE OF PERFUSION BY HIGH INTENSITY FOCUSED ULTRASOUND

(71) Applicants: Pei-Herng Hor, Houston, TX (US); Raja Muthupillai, Pearland, TX (US); Jiming Zhang, Houston, TX (US)

(72) Inventors: Pei-Herng Hor, Houston, TX (US); Raja Muthupillai, Pearland, TX (US); Jiming Zhang, Houston, TX (US)

(73) Assignees: UNIVERSITY OF HOUSTON, Houston, TX (US); ST. LUKE'S EPISCOPAL HOSPITAL, Houston, TX (US)

( * ) Notice: Subject to any disclaimer, the term of this patent is extended or adjusted under 35 U.S.C. 154(b) by 336 days.

(21) Appl. No.: 13/888,083

(22) Filed: May 6, 2013

(65) Prior Publication Data

US 2013/0317360 A1   Nov. 28, 2013

Related U.S. Application Data

(60) Provisional application No. 61/642,800, filed on May 4, 2012.

(51) Int. Cl.
*A61B 5/05* (2006.01)
*A61M 37/00* (2006.01)
(Continued)

(52) U.S. Cl.
CPC ....... *A61M 37/0092* (2013.01); *A61B 5/0036* (2018.08); *A61B 5/055* (2013.01); *A61N 7/02* (2013.01); *G01R 33/4804* (2013.01)

(58) Field of Classification Search
CPC combination set(s) only.
See application file for complete search history.

(56) References Cited

U.S. PATENT DOCUMENTS 5,810,888 A   9/1998   Fenn
7,479,483 B2   1/2009   Ponzoni et al.
(Continued)

FOREIGN PATENT DOCUMENTS

GB   2479598 A   10/2011

OTHER PUBLICATIONS

Zhang J, Mougenot C, Partanen A, Muthupillai R and Hor PH, "Volumetric Magnetic Resonance Imaging-Guided High-Intensity Focused Ultrasound for Noninvasive, In Vivo Determination of Tissue Thermal Conductivity: Initial Experience in a Pig Model", A draft of the paper and a one page conference abstract are included in Appendix A.
(Continued)

*Primary Examiner* — Jonathan Cwern
(74) *Attorney, Agent, or Firm* — Winstead PC

(57) ABSTRACT

In some embodiments, the present disclosure pertains to a method of delivery of an active agent to a target tissue, in a subject in need thereof comprising positioning a high intensity focused ultrasound transducer to enable delivery of ultrasound energy to the target tissue. Such a method comprises energizing the high intensity focused ultrasound transducer; imaging at least a portion of the target tissue; and discontinuing delivery of ultrasound energy. Further, such a method may comprise administering the active agent to the subject under the conditions of thermal stimulation. In another embodiment, the present disclosure relates to a method of treating a tumor in a subject in need thereof comprising administering a therapeutic agent to the subject and providing thermal stimulation to the tumor. In some embodiments, there is provided a method for increasing the efficacy of a therapeutic agent in a target tissue.

11 Claims, 9 Drawing Sheets

(51) Int. Cl.
*A61N 7/02* (2006.01)
*A61B 5/00* (2006.01)
*A61B 5/055* (2006.01)
*G01R 33/48* (2006.01)

(56) References Cited

U.S. PATENT DOCUMENTS

| | | | |
|---|---|---|---|
| 7,505,807 | B1 | 3/2009 | Kucharczyk et al. |
| 7,758,541 | B2 | 7/2010 | Wallace et al. |
| 7,771,418 | B2 | 8/2010 | Chopra et al. |
| 7,807,134 | B2 | 10/2010 | Safavy |
| 7,981,442 | B2 | 7/2011 | Hood et al. |
| 2003/0233085 | A1 | 12/2003 | Giammarusti |
| 2006/0206105 | A1* | 9/2006 | Chopra ............ A61B 5/055 606/27 |
| 2008/0021305 | A1* | 1/2008 | He ............ A61B 5/055 600/411 |
| 2008/0045865 | A1* | 2/2008 | Kislev ............ 601/3 |
| 2009/0112132 | A1* | 4/2009 | Chang ............ A61B 5/416 601/3 |
| 2009/0118725 | A1 | 5/2009 | Auth et al. |
| 2010/0260677 | A1* | 10/2010 | Bhatia ............ A61K 41/0052 424/489 |
| 2012/0071746 | A1* | 3/2012 | Vortman ............ A61B 5/055 600/411 |
| 2015/0080705 | A1* | 3/2015 | Partanen ............ A61B 5/055 600/411 |

OTHER PUBLICATIONS

One animal experiment depicted in Appendix B.
Zhang J, Hor PH, Fischer J, Pmianen A, Karjalainen T and R. Muthupillai, "A Temperature Dependent Perfusion Rate Model for Simulating Temperature Evolution of Tissue for Magnetic Resonance Imaging guided High Intensity Focused Ultrasound (MR-HIFU) Therapy: Initial Experience in a Pig Model", presented at International Society of Magnetic Resonance in Medicine annual meeting, ISI\IIRM, # 1662, Quebec, Canada, May ih_13th, 2011. See abstract in Appendix C.
The functional block diagram of the MRgHIFU system depicted in Appendix D.
Dragonu I et al., Non-Invasive Determination of Tissue Thermal Parameters From High Intensity Focused Ultrasound Treatment Monitored by Volumetric MRI Thermometry, NMR in Biomedicine, 22, 843,2009.
Pennes HH, Analysis of Tissue and Arterial Blood Temperatures in the Resting Human Forearm, J. Appl. Physiol. 1,93, 1948.
Zhang J, et al., Volumetric Ablation of tissue using Magnetic Resonance Imaging guided High Intensity Focused Ultrasound (MRgFUS) with feedback control and multi-slice thermal monitoring: Initial experience in a pig model, ISMRM, #4131, 2010.
Grossman L. "Reinventing the Inventor". TIME. Nov. 28, 2011, p. 74.
Jolesz A. Ference, MRI-Guided Focused Ultrasound Sugery, Annu. Rev. Med. 2009, 60, p. 417-430.
Mankoff, D. and Krohn, K, PET imaging of response and resistance to cancer therapy, Cancer Drug Resistance. 2006, p. 105-122.
Specht J. et al, Tumor Metabolisim and Blood Flow as Assessed by Positron Emission Tomorgraph Varies by Tumor Subtype in locally Advanced Breast Cancer, Clinical Cancer Research, 2010, 16(10), p. 2803-2810.

Jansen JF, Backes WH, Nicolay K, Kooi ME, $^1$H MR spectroscopy of the brain: absolute quantification of metabolites, Radiology. 2006, 240(2), p. 318-332.
Vanne A, Hynynen K., MRI feedback temperature control for focused ultrasound surgery, Phys Med Biot 2003, 48(1):31-43.
Hynynen, K, MRI guided focused ultrasound surgery, Med Phys 2002, 29(6):I329-I329.
Cline HE, et al., MR Temperature Mapping of Focused Ultrasound Surgery. Magn Reson Med, 1994, 31(6):628-636.
Ekstrand V, et al., Influence of electrical and thermal properties on RF ablation of breast cancer: is the tumour preferentially heated? Biomedical Engineering Online 2005, 4:41.
Liu Z, et al., Characterization of the RF ablation-induced 'oven effect': The importance of background tissue thermal conductivity on tissue heating, Int J Hyperthermia 2006, 22(4):327-342.
Zhu L, Lemons DE, Weinbaum S, A new approach for predicting the enhancement in the effective conductivity of perfused muscle tissue due to hyperthermia, Ann Biomed Eng 1995, 23(1):1-12.
Lang J, Erdmann B, Seebass M, Impact of nonlinear heat transfer on temperature control in regional hyperthermia, IEEE Trans Biomed Eng 1999, 46(9):1129-1138.
Zhang AL, Xu LX, Sandison GA, Zhang JY, A microscale model for prediction of breast cancer cell damage during cryosurgery, Cryobiology 2003, 47(2):143-154.
Rui J, Tatsutani KN, Dahiya R, Rubinsky B. Effect of thermal variables on human breast cancer in cryosurgery. Breast Cancer Res Tr 1999, 53(2):185-192.
Diller KR, Ryan TP, Heat transfer in living systems: Current opportunities. J Heat Transf—Trans ASME 1998, 120(4):810-829.
Telenkov SA, et al., Non-contact measurement of thermal diffusivity in tissue, Phys Med Biol 2001, 46(2):551-558.
Anand A, Kaczkowski PJ, Noninvasive measurement of local thermal diffusivity using backscattered ultrasound and focused ultrasound heating, Ultrasound Med Biol 2008, 34(9):1449-1464.
Cheng HLM, Pewes DB, Tissue thermal conductivity by magnetic resonance thermometry and focused ultrasound heating, J Magn Reson Imaging, 2002, 16(5):598-609.
Miller NR, Bamber JC, ter Haar GR, Imaging of temperature-induced echo strain: preliminary in vitro study to assess feasibility for guiding focused ultrasound surgery, Ultrasound Med Biol 2004, 30(3):345-356.
Enholm JK, et al., Improved Volumetric MR-HIFU Ablation by Robust Binary Feedback Control, IEEE Trans Biomed Eng 2010, 57(1):103-113.
Kohler MO, et al., Volumetric HIFU ablation under 3D guidance of rapid MRI thermometry. Med Phys 2009, 36(8):3521-3535.
Salomir R, Palussiere J, Vimeux FC, et al., Local hyperthermia with MRguided focused ultrasound: spiral trajectory of the focal point optimized for temperature uniformity in the target region, J Magn Reson Imaging, 2000; 12(4):571-583.
El-Sharkawy AM, Schar M, Bottomley PA, Atalar E., Monitoring and correcting spatio-temporal variations of the MR scanner's magnetic field, MAGMA 2006, 19(5):223-236.
Chang W. Song, IEEE transaction on biomedical engineering, 31(1), 9-16, 1984.
Zhang J et al., Non-invasive Estimation of Tissue Thermal Conductivity from Spatio-temporal Temperatures Profiles of Volumetric Sonications Using Magnetic Resonance Imaging Guided High Intensity Focused Ultrasound (MR-HIFU) Therapy: Initial Experience in a Pig Model. 2nd MRgFUS symposium 2010, P21.

\* cited by examiner

US 10,441,769 B2

TARGETED DELIVERY OF ACTIVE AGENTS USING THERMALLY STIMULATED LARGE INCREASE OF PERFUSION BY HIGH INTENSITY FOCUSED ULTRASOUND

CROSS-REFERENCE TO RELATED APPLICATIONS

This application claims priority to U.S. Provisional Application No. 61/642,800, filed May 4, 2012. The entirety of the aforementioned application is incorporated herein by reference.

FIELD

This invention relates to targeted delivery of an active agent using thermally stimulated large increase of perfusion.

BACKGROUND

Targeted delivery of an active agent provides for an increased concentration of the active agent in some parts of the body relative to others. Current methods for targeted delivery, of an active agent, have numerous limitations in terms of efficacy and affectivity. Therefore, there is a need to develop more effective methods of targeted delivery.

SUMMARY

This invention describes a method that uses thermally stimulated large increase of perfusion (TSLIP) for targeted drug delivery. For example, in one non-limiting embodiment, TSLIP may be induced by spatially targeted ultrasound, e.g., using magnetic resonance imaging guided high intensity focused ultrasound or conventional ultrasound for targeted drug delivery. The concept can also be used to develop new heat/mechanical vibration activated drugs or deploy existing heat/mechanical vibration activated drugs for target-specific drug delivery and therapy. In some embodiments, the present disclosure pertains to a method of delivery of an active agent to a target tissue, in a subject in need thereof. Such a method may comprise the step of identifying the target tissue in the subject. In some embodiments, the method further comprises positioning a high intensity focused ultrasound transducer to enable delivery of ultrasound energy to the target tissue. Such a method may also comprise energizing the high intensity focused ultrasound transducer to thermally stimulate the target tissue; imaging at least a portion of the target tissue that includes the volume of the target tissue being thermally stimulated; and discontinuing delivery of ultrasound energy when said target tissue achieves a pre-determined set temperature or temperature profile. Further, such a method may comprise administering the active agent to the subject under the conditions of thermal stimulation. In some embodiments, the thermal stimulation may induce a temperature dependent large increase of blood perfusion to the target tissue.

In another embodiment, the present disclosure relates to a method of treating a tumor in a subject in need thereof comprising the steps of administering a therapeutic agent to the subject; and providing thermal stimulation to the tumor. In some embodiments, the present disclosure provides for the thermal stimulation inducing a large increase of blood perfusion to the tumor. In a related embodiment, a disproportionate amount of active agent to accumulate in the tumor as a result of the thermally-stimulated large increase in perfusion.

In yet, another embodiment, there is provided a method for increasing the efficacy of a therapeutic agent in a target tissue, in a subject in need thereof, comprising the steps of administering a therapeutic agent to the subject; and providing thermal stimulation to the target tissue. Such a method results in a large increase of blood perfusion to the target tissue. In some embodiments, a disproportionate amount of active agent accumulates in the target tissue as a result of the thermally-stimulated large increase of blood perfusion.

The above objects and other objects, features, and advantages of the present disclosure are readily apparent from the following detailed description of the best mode for carrying out the invention when taken in conjunction with the accompanying drawings.

BRIEF DESCRIPTION OF THE DRAWINGS

In order that the manner in which the above recited and other advantages and objects of the invention are obtained, a more particular description of the invention briefly described above will be rendered by reference to specific embodiments thereof, which are illustrated in the appended Figures. Understanding that these Figures depict only typical embodiments of the invention and are therefore not to be considered limiting of its scope, the invention will be described with additional specificity and detail through the use of the accompanying Figures in which.

DETAILED DESCRIPTION

Figure 1:
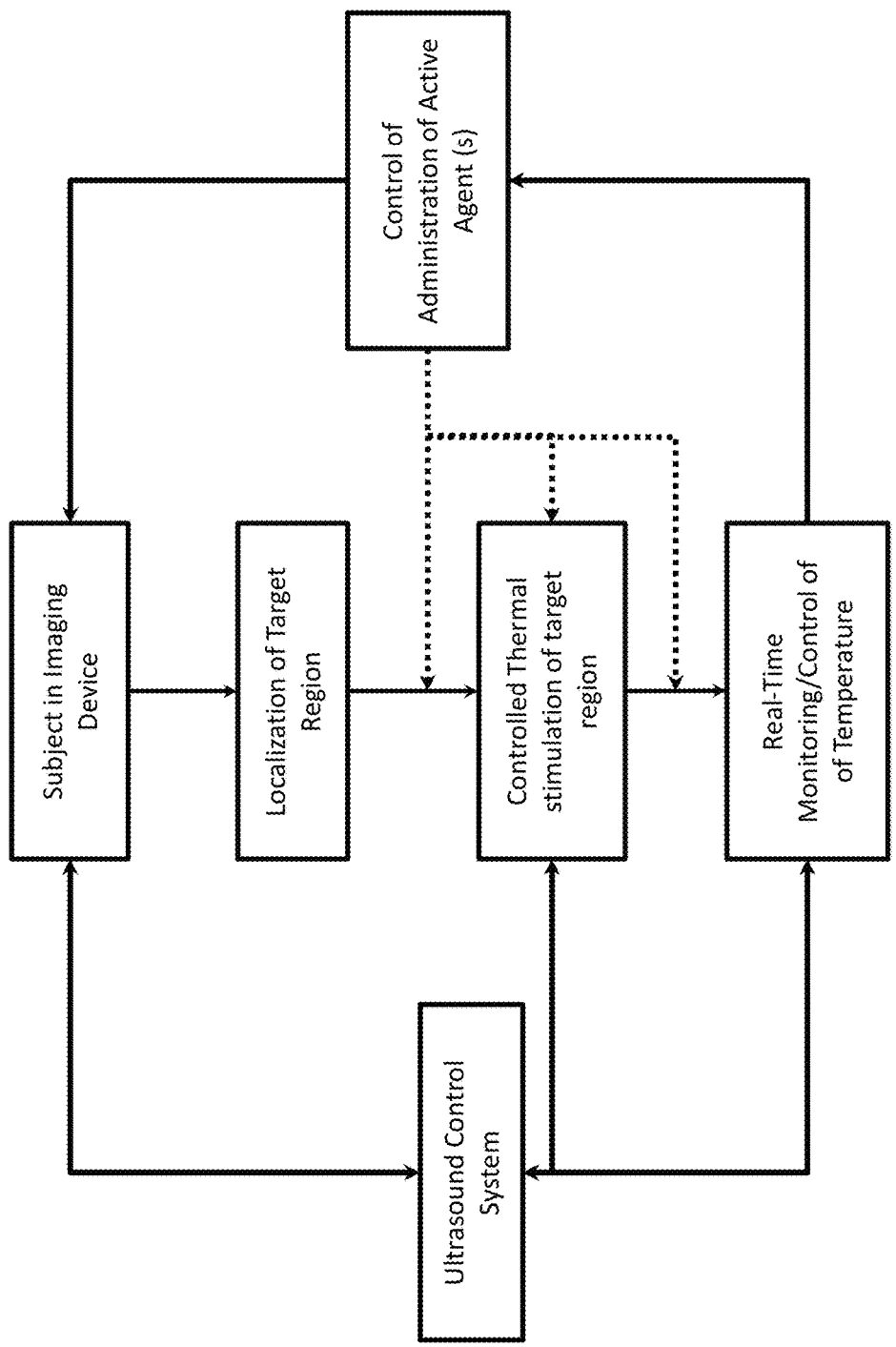
FIG. 1. shows a flow diagram representative of an embodiment of the present disclosure. The subject is placed within the imaging platform as shown. The imaging platform provides for the localization of the region that needs to be thermally stimulated. In some embodiments, the imaging device may also serve to measure and monitor the resulting rise in temperature. In an example, this information may be used to control the High Intensity Focused Ultrasound (HIFU) device. Active agent(s) may be administered before, during, or after attainment of a pre-defined thermal or biochemical profile. Such a method may also use the imaging device to confirm the effectiveness of target localization and active agent delivery via subsequent imaging.

It is to be understood that both the foregoing general description and the following detailed description are exemplary and explanatory only, and are not restrictive of the invention, as claimed. In this application, the use of the singular includes the plural, the word "a" or "an" means "at least one", and the use of "or" means "and/or", unless specifically stated otherwise. Furthermore, the use of the term "including", as well as other forms, such as "includes" and "included", is not limiting. Also, terms such as "element" or "component" encompass both elements or components comprising one unit and elements or components that comprise more than one unit unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated herein by reference in their entirety for any purpose. In the event that one or more of the incorporated literature and similar materials defines a term in a manner that contradicts the definition of that term in this application, this application controls.

As used herein, the term "Magnetic Resonance Imaging (MRI)" refers to a medical imaging technique most commonly used in radiology to visualize the internal structure and function of the body. MRI provides much greater contrast between the different soft tissues of the body than computed tomography (CT) does, making it especially useful in neurological (brain), musculoskeletal, cardiovascular, and oncological (cancer) imaging. Unlike CT, it uses non-ionizing radiation, but uses a powerful magnetic field to align the nuclear magnetization of (usually) hydrogen atoms in water in the body. Radio frequency (RF) fields are used to systematically alter the alignment of this magnetization, causing the hydrogen nuclei to produce a rotating magnetic field detectable by the scanner. This signal can be manipulated by additional magnetic fields to build up enough information to construct an image of the body.

As used herein an "Active Agent" may be a therapeutic agent, an imaging agent or a combination thereof. An active agent may be an agent that provides dual function as diagnostic (e.g., via imaging) and therapeutic (e.g., via heat/mechanical activation) agents. The active agent may be any appropriate agent that may be released from a particle containing it. The selection of the active agent depends on the application. An "Active Agent" may also refer to a composition that possesses a biologically relevant activity or property. Biologically relevant activities are activities associated with biological reactions or events or that allows the detection, monitoring, or characterization of biological reactions or events. Biologically relevant activities include, but are not limited to, therapeutic activities (e.g., the ability to improve biological health or prevent the continued degeneration associated with an undesired biological condition), targeting activities (e.g., the ability to bind or associate with a biological molecule or complex), monitoring activities (e.g., the ability to monitor the progress of a biological event or to monitor changes in a biological composition), imaging activities (e.g., the ability to observe or otherwise detect biological compositions or reactions), and signature identifying activities (e.g., the ability to recognize certain cellular compositions or conditions and produce a detectable response indicative of the presence of the composition or condition). The active agents of the present invention are not limited to these particular illustrative examples. Indeed any useful active agent may be used including agents that deliver or destroy biological materials, cosmetic agents, and the like.

As used herein "Therapeutic Agent" may be any physiologically or pharmacologically active substance that may produce a desired biological effect in a targeted site in an animal, such as a mammal or a human. The therapeutic agent may be any inorganic or organic compound, without limitation, including peptides, proteins, nucleic acids, and small molecules, any of which may be characterized or uncharacterized. The therapeutic agent may be in various forms, such as an unchanged molecule, molecular complex, pharmacologically acceptable salt, such as hydrochloride, hydrobromide, sulfate, laurate, palmitate, phosphate, nitrite, nitrate, borate, acetate, maleate, tartrate, oleate, salicylate, and the like. For acidic therapeutic agent, salts of metals, amines or organic cations, for example, quaternary ammonium may be used. Derivatives of drugs, such as bases, esters and amides also may be used as a therapeutic agent. A therapeutic agent that is water insoluble may be used in a form that is a water soluble derivative thereof, or as a base derivative thereof, which in either instance, or by its delivery, is converted by enzymes, hydrolyzed by the body pH, or by other metabolic processes to the original therapeutically active form.

The therapeutic agent may be a chemotherapeutic agent, an immunosuppressive agent, a cytokine, a cytotoxic agent, a nucleolytic compound, a radioactive isotope, a receptor, and a pro-drug activating enzyme, which may be naturally occurring or produced by synthetic or recombinant methods, or any combination thereof.

Drugs that are affected by classical multidrug resistance, such as vinca alkaloids (e.g., vinblastine and vincristine), the anthracyclines (e.g., doxorubicin and daunorubicin), RNA transcription inhibitors (e.g., actinomycin-D) and microtubule stabilizing drugs (e.g., paclitaxel) may have particular utility as the therapeutic agent.

A cancer chemotherapy agent may be a preferred therapeutic agent. Useful cancer chemotherapy drugs include nitrogen mustards, nitrosorueas, ethyleneimine, alkane sulfonates, tetrazine, platinum compounds, pyrimidine analogs, purine analogs, antimetabolites, folate analogs, anthracyclines, taxanes, vinca alkaloids, topoisomerase inhibitors and hormonal agents. Exemplary chemotherapy drugs are Actinomycin-D, Alkeran, Ara-C, Anastrozole, Asparaginase, BiCNU, Bicalutamide, Bleomycin, Busulfan, Capecitabine, Carboplatin, Carboplatinum, Carmustine, CCNU, Chlorambucil, Cisplatin, Cladribine, CPT-11, Cyclophosphamide, Cytarabine, Cytosine arabinoside, Cytoxan, Dacarbazine, Dactinomycin, Daunorubicin, Dexrazoxane, Docetaxel, Doxorubicin, DTIC, Epirubicin, Ethyleneimine, Etoposide, Floxuridine, Fludarabine, Fluorouracil, Flutamide, Fotemustine, Gemcitabine, Herceptin, Hexamethylamine, Hydroxyurea, Idarubicin, Ifosfamide, Irinotecan, Lomustine, Mechlorethamine, Melphalan, Mercaptopurine, Methotrexate, Mitomycin, Mitotane, Mitoxantrone, Oxaliplatin, Paclitaxel, Pamidronate, Pentostatin, Plicamycin, Procarbazine, Rituximab, Steroids, Streptozocin, STI-571, Streptozocin, Tamoxifen, Temozolomide, Teniposide, Tetrazine, Thioguanine, Thiotepa, Tomudex, Topotecan, Treosulphan, Trimetrexate, Vinblastine, Vincristine, Vindesine, Vinorelbine, VP-16, and Xeloda.

Useful cancer chemotherapy drugs also include alkylating agents, such as Thiotepa and cyclosphosphamide; alkyl sulfonates such as Busulfan, Improsulfan and Piposulfan; aziridines such as Benzodopa, Carboquone, Meturedopa, and Uredopa; ethylenimines and methylamelamines including altretamine, triethylenemelamine, trietylenephosphoramide, triethylenethiophosphaoramide and trimethylolomelamine; nitrogen mustards such as Chlorambucil, Chlomaphazine, Cholophosphamide, Estramustine, Ifosfamide, mechlorethamine, mechlorethamine oxide hydrochloride, Melphalan, Novembiehin, Phenesterine, Prednimustine, Trofosfamide, uracil mustard; nitroureas such as Cannustine, Chlorozotocin, Fotemustine, Lomustine, Nimustine, and Ranimustine; antibiotics such as Aclacinomysins, Actinomycin, Authramycin, Azaserine, Bleomycins, Cactinomycin, Calicheamicin, Carabicin, Caminomycin, Carzinophilin, Chromoinycins, Dactinomycin, Daunorubicin, Detorubicin, 6-diazo-5-oxo-L-norleucine, Doxorubicin, Epirubicin, Esorubicin, Idambicin, Marcellomycin, Mitomycins, mycophenolic acid, Nogalamycin, Olivomycins, Peplomycin, Potfiromycin, Puromycin, Quelamycin, Rodorubicin, Streptonigrin, Streptozocin, Tubercidin, Ubenimex, Zinostatin, and Zorubicin; anti-metabolites such as Methotrexate and 5-fluorouracil (5-FU); folic acid analogues such as Denopterin, Methotrexate, Pteropterin, and Trimetrexate; purine analogs such as Fludarabine, 6-mercaptopurine, Thiamiprine, and Thioguanine; pyrimidine analogs such as Ancitabine, Azacitidine, 6-azauridine, Carmofur, Cytarabine, Dideoxyuridine, Doxifluridine, Enocitabine, Floxuridine, and 5-FU; androgens such as Calusterone, Dromostanolone Propionate, Epitiostanol, Rnepitiostane, and Testolactone; anti-adrenals such as aminoglutethimide, Mitotane, and Trilostane; folic acid replenisher such as frolinic acid; aceglatone; aldophosphamide glycoside; aminolevulinic acid; Amsacrine; Bestrabucil; Bisantrene; Edatraxate; Defofamine; Demecolcine; Diaziquone; Elformithine; elliptinium acetate; Etoglucid; gallium nitrate; hydroxyurea; Lentinan; Lonidamine; Mitoguazone; Mitoxantrone; Mopidamol; Nitracrine; Pentostatin; Phenamet; Pirarubicin; podophyllinic acid; 2-ethylhydrazide; Procarbazine; PSK®; Razoxane; Sizofrran; Spirogermanium; tenuazonic acid; triaziquone; 2,2',2"-trichlorotriethylamine; Urethan; Vindesine; Dacarbazine; Mannomustine; Mitobronitol; Mitolactol; Pipobroman; Gacytosine; Arabinoside ("Ara-C"); cyclophosphamide; thiotEPa; taxoids, e.g., Paclitaxel (TAXOL®, Bristol-Myers Squibb Oncology, Princeton, N.J.) and Doxetaxel (TAXOTERE®, Rhone-Poulenc Rorer, Antony, France); Chlorambucil; Gemcitabine; 6-thioguanine; Mercaptopurine; Methotrexate; platinum analogs such as Cisplatin and Carboplatin; Vinblastine; platinum; etoposide (VP-16); Ifosfamide; Mitomycin C; Mitoxantrone; Vincristine; Vinorelbine; Navelbine; Novantrone; Teniposide; Daunomycin; Aminopterin; Xeloda; Ibandronate; CPT-11; topoisomerase inhibitor RFS 2000; difluoromethylomithine (DMFO); retinoic acid; Esperamicins; Capecitabine; and pharmaceutically acceptable salts, acids or derivatives of any of the above. Also included are anti-hormonal agents that act to regulate or inhibit hormone action on tumors such as anti-estrogens including for example Tamoxifen, Raloxifene, aromatase inhibiting 4(5)-imidazoles, 4 Hydroxytamoxifen, Trioxifene, Keoxifene, Onapristone, And Toremifene (Fareston); and anti-androgens such as Flutamide, Nilutamide, Bicalutamide, Leuprolide, and Goserelin; and pharmaceutically acceptable salts, acids or derivatives of any of the above.

Cytokines may be also used as the therapeutic agent. Examples of such cytokines are lymphokines, monokines, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet growth factor; transforming growth factors (TGFs) such as TGF-α and TGF-β; insulin-like growth factor-I and -II; erythropoietin (EPO); osteoinductive factors; interferons such as interferon-α, -β and -γ; colony stimulating factors (CSFs) such as macrophage-CSF (M-CSF); granulocyte-macrophage-CSF (GM-CSF); and granulocyte-CSF (GCSF); interleukins (ILs) such as IL-1, IL-1a, IL-2, IL-3, IL-4, IL-5, IL-6, IL-7, IL-8, IL-9, IL-11, IL-12, IL-15; a tumor necrosis factor such as TNF-α or TNF-β; and other polypeptide factors including LIF and kit ligand (KL). As used herein, the term cytokine includes proteins from natural sources or from recombinant cell culture and biologically active equivalents of the native sequence cytokines.

For a more detailed description of anticancer agents and other therapeutic agents, those skilled in the art are referred to any number of instructive manuals including, but not limited to, the Physician's Desk Reference and to Goodman and Gilman's "Pharmacological Basis of Therapeutics" tenth edition, Eds. Hardman et al., 2001.

As used herein "Diagnostic Agent" may be any substance that provides imaging information or physiological information about a targeted site in a body of an animal, such as a mammal or a human being. The diagnostic agent may comprise magnetic material, such as iron oxide, for magnetic resonance imaging. The diagnostic agent may be also an ultrasound contrast agent, such as a micro or nanobubble or iron oxide micro or nanoparticle.

As used herein, the terms "treat," "treatment" and "treating" shall be given their ordinary meaning and shall refer to the reduction or amelioration of the progression, severity, and/or duration of a pathological condition or a symptom thereof.

As used herein, the term "Subject" includes animals and humans requiring intervention or manipulation due to a disease state, treatment regimen or experimental design.

Thermally Stimulated Large Increase of Perfusion

Heating tissues in vivo can induce a fast physiological response of increased blood perfusion to counter the temperature rise. This may be referred to as thermally stimulated large increase of perfusion (TSLIP) herein. TSLIP-mediated therapy utilizes the thermally stimulated large increase of perfusion to the target tissue to increase the amount of a therapeutic or a diagnostic agent delivered to a target tissue. TSLIP-mediated therapy may also be used to enhance the therapeutic effects of the active agent.

Mechanisms

In general, TSLIP-mediated therapy may act via numerous mechanisms to increase the delivery of a therapeutic or diagnostic agent and enhance the therapeutic effects of an active agent. In some embodiments creating a differential blood-flow to a specific region of the anatomy by heating, provides the mechanism for increasing the availability of therapeutic or diagnostic agent to the tissue of interest. This increased availability may be used to enhance (a) either the visualization of the agent for diagnostic purposes, and/or (b) used as a therapeutic agent for the treatment. In a related embodiment, the agent administered may either be a generic systemic agent or a tailored agent.

In an embodiment, of the present disclosure the active agent may be tailored such that it becomes active only upon exposure to heat or mechanical vibrations or both. In other embodiments, the active agent may be tailored to bind to a specific molecular target via a targeting moiety.

"Targeting moiety" is any factor that may facilitate targeting of a specific site by an active agent. For example, the targeting moiety may be a chemical targeting moiety, a physical targeting moiety, a geometrical targeting moiety or a combination thereof. The chemical targeting moiety may be a chemical group or molecule on a surface of the active agent; the physical targeting moiety may be a specific physical property of the active agent, such as a surface or hydrophobicity; the geometrical targeting moiety includes a size and a shape of the active agent. The active agent may be contained in a particle. The targeting moiety may be on the surface of a particle used to deliver the active agent.

The "Particle" used to deliver the active agent may be a lipid based particle, such as a liposome, a micelle or lipid encapsulated perfluorocarbon emulsion; an ethosome; a carbon nanotube, such as single wall carbon nanotube; a fullerene nanoparticle; a metal nanoparticle, such gold nanoshell or triangular silver nanoparticle; a semiconductor nanoparticle, such as quantum dot or boron doped silicon nanowire; a polymer nanoparticle, such as particles made of biodegradable polymers and ion doped polyacrylamide particles; an oxide nanoparticle, such as iron oxide particle, a polymer coated iron oxide nanoparticle or a silicon oxide particle; a viral particle, such as an engineered viral particle or an engineered virus-polymer particle; a polyionic particle, such as leashed polycations; a ceramic particle, such as silica based ceramic nanoparticles, or a combination thereof. In some embodiments, the particle is a nucleic acid nanoparticle, such as a small interfering RNA (siRNA) particle. In all embodiments, the differential blood flow would work advantageously to make the active agent or the tailored active agent disproportionately available in the targeted region of interest.

Administration of the active agent may be systemic or local. The majority of therapeutic or diagnostic applications may involve some type of parenteral administration, which includes intravenous (i.v.), intramuscular (i.m.) and subcutaneous (s.c.) injection. The non-parenteral examples of local administration include intramuscular and subcutaneous injections. Intravascular administration may be either local or systemic.

Hyperthermia is known to enhance drug therapeutic effect and TSLIP-mediated therapy goes beyond the conventional hyperthermia approach by selectively exploiting the associated large increase in regional perfusion for targeted delivery of active agents. In some embodiments, both elevated temperature and mechanical vibrations due to ultrasound may potentially enhance drug therapeutic effects.

In some embodiments, the mechanism may involve creating an agent (therapeutic or diagnostic) that is thermally/mechanically sensitive such that it becomes 'active' upon being exposed to heat and/or mechanical vibration. This activity may be used for diagnostic purposes for visualizing the region of the agent's activity by concurrently acquired diagnostic images, or for therapeutic purposes for enhancing the effectiveness of the drug.

Thermal dosage delivered by thermal stimulation by itself may be therapeutic. Therefore, the combination of thermal treatment and TSLIP-mediated targeted drug delivery may provide an extra degree of freedom for optimal therapy. In some embodiments, the mechanism may involve combining thermal treatment and TSLIP-mediated targeted delivery of the therapeutic or diagnostic agent. For instance, thermal ablation used together with chemotherapy may treat tumor more effectively than either of the technique used alone.

In some embodiments of the present disclosure, TSLIP-mediated therapy may provide for targeted and effective delivery of an active agent via the aforementioned mechanisms either independently or in combination.

TSLIP-mediated therapy has multiple layers of application starting from simply increasing and targeting drug delivery to more complex thermal/mechanical therapeutic enhancement effects. TSLIP-mediated therapy may be developed into a targeted drug delivery system with real time drug effects evaluation capability. The system is non-invasive and can be used repeatedly as needed.

In some embodiments the present disclosure relates to a method of delivery of an active agent to a target tissue, in a subject in need thereof, comprising identifying the target tissue; positioning a high intensity focused ultrasound transducer; energizing the high intensity focused ultrasound transducer to thermally stimulate the target tissue; imaging at least a portion of the target tissue that includes the volume of the target tissue being stimulated; discontinuing delivery of ultrasound energy when said target tissue achieves a pre-determined set temperature and/or temperature profile; and administering the active agent to the subject, where the ultrasound stimulates a temperature dependent large increase of blood perfusion to the target tissue. In some embodiments the target tissue may be identified using Magnetic Resonance Imaging (MRI). In a related embodiment, the identification of the target tissue may be by using conventional ultrasound. In an embodiment, of the present disclosure the high intensity focused ultrasound transducer may be positioned by placing it over the target tissue. In an alternative embodiment, the transducer may be placed within the cavity of the target tissue. For instance, in an exemplary embodiment, the transducer may be placed within an artery to thermally stimulate pulmonary veins for treatment of arrhythmias or within a body cavity such as the rectum to treat a pathological condition in the prostate.

In some embodiments the frequency of energy supplied by the high intensity focused ultrasound transducer may be ranging from about 0.8 MHz and about 4.0 MHz. Further, in some embodiments, the step of subsequently imaging at least a portion of the target tissue may be by magnetic resonance imaging. In a related embodiment the imaging may measure the temperature distribution within the target tissue of the subject. Target tissue temperatures may range from about 39° C. to about 99° C., during thermal stimulation. In an embodiment, the present disclosure provides for using the temperature distribution thus obtained to control the delivery of the high intensity focused ultrasound to the target tissue. In some embodiments the present disclosure provides that the target tissue may be a pathological tissue.

In some embodiments, the present disclosure provides for the active agent to be administered simultaneously with the step of energizing the high intensity focused ultrasound transducer. In other embodiments, the active agent may be administered before the step of energizing the high intensity focused ultrasound transducer. In some embodiments, the active agent may be designed to be activated by heat or by mechanical vibrations or by both. In some embodiments, the active agent may comprise a targeting moiety specific for the target tissue. In some embodiments the targeting moiety may be on the surface of the active agent. In other embodiments, the targeting moiety may be present on the surface of a particle containing the active agent. In some embodiments, the present disclosure relates to the administration of the active agent by vascular route.

In some embodiments, the present disclosure provides a method of treating a tumor in a subject in need thereof comprising the steps of administering a therapeutic agent to the subject; and providing thermal stimulation to the tumor, where the thermal stimulation results in a large increase of blood perfusion to the tumor causing a disproportionate amount of active agent to accumulate in the tumor. In a related embodiment, the thermal stimulation is provided by Magnetic Resonance guided high intensity focused ultrasound. The thermal energy provided in such a method may also be designed to induce thermal ablation of the tumor.

In another embodiment, the present disclosure relates to a method for increasing the efficacy of a therapeutic agent in a target tissue, in a subject in need thereof, comprising the steps of administering a therapeutic agent to the subject; and providing thermal stimulation to the target tissue, where the thermal stimulation results in a large increase of blood perfusion to the target tissue causing a disproportionate amount of active agent to accumulate in the target tissue. In a related embodiment, the thermal stimulation is provided by Magnetic Resonance guided high intensity focused ultrasound. In some embodiments, the therapeutic agent may comprise a targeting moiety specific for the target tissue. In some embodiments the targeting moiety may be on the surface of the therapeutic agent. In other embodiments, the targeting moiety may be present on the surface of a particle containing the therapeutic agent.

As set forth in more detail herein, the systems and methods of the present disclosure have numerous embodiments and variations. In particular, the systems and methods of the present disclosure may use thermally stimulated large increase of blood perfusion by magnetic resonance imaging guided high intensity focused ultrasound for targeted drug delivery (TSLIP-MRgHIFU). Additionally, the systems and methods of the present disclosure may also be used to develop thermally/mechanically activated drugs for targeted drug delivery. Likewise, the systems and methods of the present disclosure may also be used with drug delivery with other imaging guidance systems like ultrasound, or without image guidance. In some embodiments, the present disclosure relates to methods that seek to exploit the inordinate increase in blood flow due to thermal stimulation as a potentiating mechanism for 'theranostic' (therapeutic or diagnostic) agent delivery.

Clinical Techniques for Targeted Heating of Tissue

Substantial increase in local blood flow may be accomplished with targeted heating of tissue by a number of clinical techniques. For instance, non-invasive heating via focused ultrasound, or minimally invasive procedures such as laser ablation, or radio-frequency ablation, or even by invasive surgery may be used. However, these methods are fraught with problems, and their invasive nature imposes additional burdens of morbidity.

Magnetic resonance Imaging (MRI) guided high intensity focused ultrasound (MRgHIFU) surgery is a noninvasive thermal ablation method that uses MRI for precise target definition, treatment planning, and closed-loop control of ultrasound energy delivery. MRgHIFU is a hybrid technology combining High Intensity Focused Ultrasound (HIFU) with Magnetic Resonance Imaging. HIFU is used to kill specific tissues, for example breast tumors, deep within the body and without harm to intervening normal healthy tissues. Magnetic Resonance Imaging guidance allows the tumor to be visualized and targeted, and allows focusing of the ultrasound beam on the tumor or pathological tissue and not the normal tissue. Additionally MRI provides a means to measure tissue temperatures in real time. MRI-based methods are unencumbered by constraints related to penetration depth and can span relatively large thermodynamic range (0° C. to 100° C.). MRgHIFU technology aims to offer efficient and safe thermal ablation of targeted tumors or other pathological tissues, while preserving healthy surrounding structures. High intensity ultrasound is effective for use in treating localized cancers or other pathologies. For this purpose, the high intensity focused ultrasound (HIFU) is administered.

In order to steer and focus the therapeutic ultrasound, such an ultrasound head or device typically has multiple ultrasound emitters (transducers) arranged and operated in an array.

In general terms, magnetic resonance guiding or monitoring of such therapy takes place by administering HIFU to the subject in the examination region of a magnetic resonance scanner. Magnetic resonance data are acquired in a known manner from the subject in the scanner while the ultrasound therapy is in progress. In real-time with the therapy, magnetic resonance thermometry images of the subject are generated, showing the temperature distribution within a designated region of the patient. The resulting MR thermometry image can be shown on a monitor in real-time during the therapy for visual review and manual control of the therapy by a physician or a technician, or known image processing techniques can be used in order to generate appropriate extractions of information from the thermometry image for use in automatic control of the therapy. See FIG. 6.

An overview of MR-guided High Intensity Focused Ultrasound hyperthermia is described in "Hyperthermia by MR-guided Focused Ultrasound: Accurate Temperature Control Based on Fast MRI and A Physical Model of Local Energy Deposition and Heat Conduction," Salomir et al., Magnetic Resonance in Medicine, Vol. 43 (2000) pages 342-347, and Zhang J et al., 2013, 37(4): 950-957. Various automatic control techniques are described, for example, in "Automatic Spatial and Temporal Temperature Control for MR-Guided Focused Ultrasound Using Fast 3D MR Thermometry and Multispiral Trajectory of the Focal Point," Mougenot et al., Magnetic Resonance in Medicine, Vol. 52 (2004) pgs 1005-1015; "Three-Dimensional Spatial and Temporal Temperature Control with MR Thermometry-Guided Focused Ultrasound (MRgHIFU)," Mougenot et al., Magnetic Resonance in Medicine, Vol. 61 (2009) pgs 603-614 and "Curvilinear Transurethral Ultrasound Applicator for Selective Prostrate Thermal Therapy," Ross et al., Medical Physics, Vol. 32, No. 6 (2005) pgs 1555-1565.

MRgHIFU surgery is quickly emerging as a real time non-invasive precision surgical resection procedure for the treatment such as uterine fibroids, breast, liver, prostate and brain cancers. For example, in a non-limiting embodiment, TSLIP controlled by magnetic resonance imaging guided high intensity focused ultrasound (TSLIP-MRgHIFU) may be used as a method for targeted drug delivery and guided therapy for treating cancerous or other pathological tissues.

Applications

In some embodiments, the present disclosure relates to a method of increasing targeted delivery of an agent to a tissue using TSLIP-MRgHIFU. MRgHIFU, due to the extra degrees of freedom provides by the HIFU, presents unique opportunities for diagnostic and fundamental experimental tools for both medical and biological research. The present disclosure relates to using TSLIP-MRgHIFU technique to attain the goal of targeted delivery of a therapeutic or a diagnostic agent and achieve guided therapy. In an embodiment of the present disclosure, TSLIP-MRgHIFU optimizes the ultrasound energy delivery and reduces the treatment time for MRgHIFU surgery.

In some embodiments, the present disclosure provides for using the TSLIP-MRgHIFU technique for targeted delivery of a therapeutic or diagnostic agent. In some embodiments, this method relates to simultaneous monitoring of the temperature elevation using imaging techniques such as magnetic resonance imaging (MRI). For instance, in an embodiment, MRgHIFU is used for real-time temperature monitoring via MR and for the simultaneous monitoring of the region of thermal dose delivery and the subsequent modulation of perfusion. The combination of administration of both the therapeutic drug, as well as an MR contrast medium, once the target temperature or temperature profile is reached, may yield a direct estimation of the increase in local perfusion that may be measured with MR imaging techniques In another embodiment of the present disclosure, the TSLIP-MRgHIFU approach may use an active agent that is designed to be therapeutic and also serves as a contrast agent for the imaging modality, for effective therapy and monitoring. For instance, the therapeutic drug may be designed to have its magnetic resonance relaxivity that can be modulated by temperature or by varying the amount of access to nearby water molecules.

In one implementation, for example, when such restricted access to mobile water molecules is removed by heating, or mechanical vibration, these spatial location of these contrast agents becomes conspicuous in MR images. This allows for a real-time visualization of drug delivery and may provide additional control for effective TSLIP mediated therapy.

In some embodiments the methods disclosed herein may be used either for the treatment or imaging or both of malignancies including prostate carcinoma, breast carcinoma, hepatocellular carcinoma, renal cell carcinoma, urinary bladder carcinoma, pancreas cancer, and osteosarcoma. In related embodiments, the methods disclosed herein may also be used either for the treatment or imaging or both of other non-vascular pathological conditions not relating to malignancy such as benign prostate hypertrophy, uterus fibroids, fibroadenoma (breast, liver). In other embodiment, the methods disclosed herein may be used for either the treatment or imaging or both of atherosclerotic plaque, thrombolysis or vascular malformations.

Thermal Properties of Tissues

For the successful clinical application of ablative procedures involving focused ultrasound, radiofrequency energy, hyperthermia, and cryogenics, physicians must be able to create lesions accurately by either heating or freezing tissue. The success of these ablative procedures largely depends on the thermal properties and physiologic responses of tissues in the targeted area. An accurate knowledge of tissue thermal properties (such as thermal conductivity, specific heat, and blood perfusion rate) and of how these properties depend on temperature used for these procedures, is necessary for understanding and controlling heat transfer in living tissue.

Figure 7:
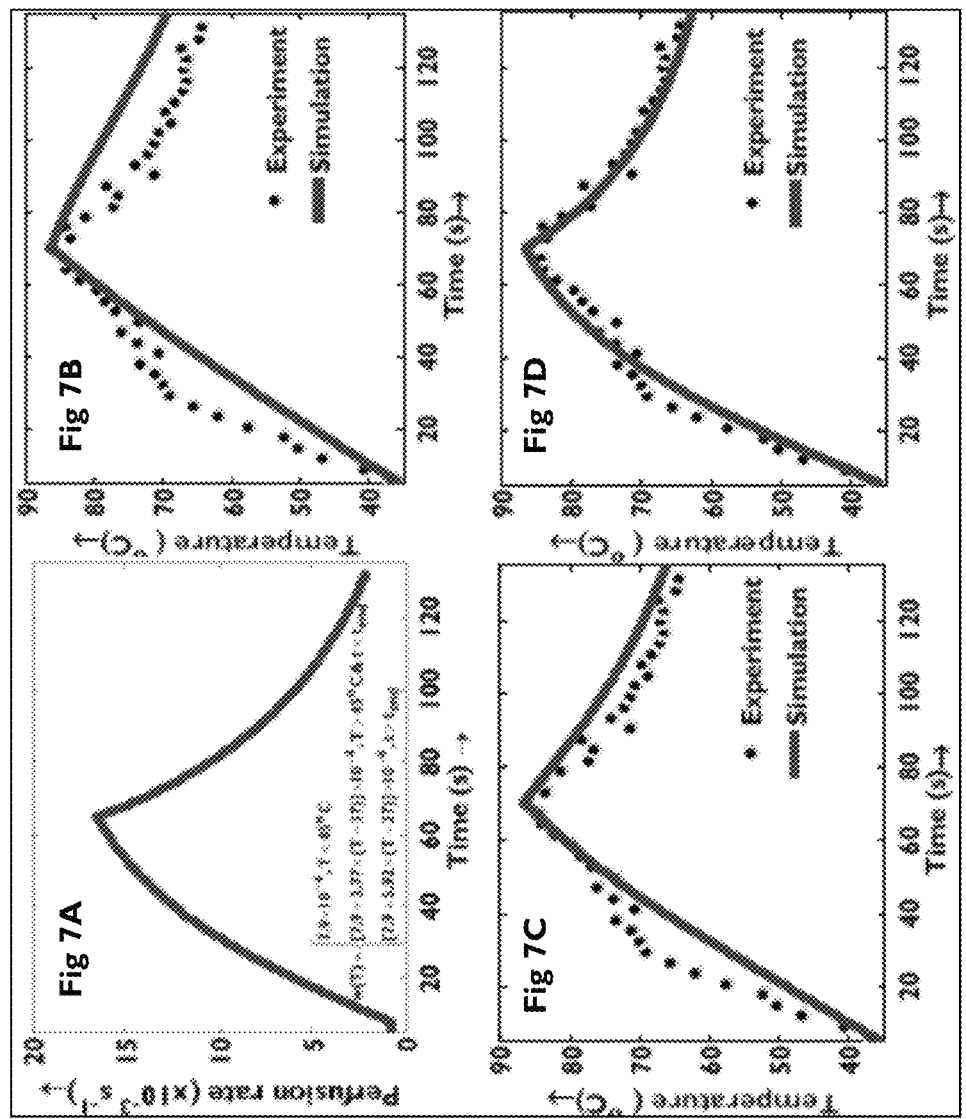
FIG. 7A represents the effect of perfusion contribution in mediating temperature evolution.
FIGS. 7B-7D represents the relative contribution of thermal conductivity and perfusion under different models disclosed herein. Three models were considered to fit the in vivo measured temperature profile, in pig skeletal muscle, with various assumptions about thermal conductivity and perfusion. In model 1, constant thermal conductivity and perfusion were assumed throughout the treatment (FIG. 7B). In model 2, a temperature dependent thermal conductivity and constant perfusion rate were assumed (FIG. 7C). In model 3, in vivo measured constant thermal conductivity and temperature dependent perfusion were used to fit the measured in vivo temperature evolution during MRgHIFU. The fitted model parameters are shown in FIG. 7A.

The success of TSLIP-MRgHIFU method disclosed herein may depend on various biophysiological parameters of target tissue as compared to normal tissue. Such parameters may include microvascular blood flow rate, thermal conductivity, and response to temperature variations of the target and the normal tissues in patients. For instance, numerical simulations, based on bio-heat transfer equation, to analyze the temperature profile data collected from animal, clinical trials designed to validate the volumetric ablation of the tissues using MRgHIFU showed that the blood perfusion rate may reach 20 times larger than the normal blood perfusion rate (FIG. 7).

Modern techniques such as infrared imaging, ultrasonography, and magnetic resonance imaging (MRI) have been used to noninvasively measure the thermal conductivity of epidermis on Caucasian adult's arm, breast of turkey, and thigh muscle of rabbit, respectively. However, these methods of measuring thermal conductivity are fraught with problems. As discussed above, infrared imaging is restricted to superficial applications because its penetration depth (which is wavelength-dependent) is only a few millimeters. Ultrasound-based methods are also limited, as the relationship between temperature and the ultrasound wave speed is linear only within a narrow change range (0~15° C.). In contrast, MRI-based methods are unencumbered by constraints related to the depth of penetration and can span a relatively large thermodynamic range (0° C. to 100° C.). A key advantage of using MRI as an in vivo temperature measurement tool is the simultaneous availability of spatial and temporal distribution of temperature. These parameters may be used to extrapolate information such as tissue thermal conductivity in vivo (FIG. 5).

Advantages

Complex system diseases, such as cancer, require multiple predicators to arrive at a statistically significant diagnosis. As cancer treatment moves toward more targeted therapy, there is an increasing need for tools to guide therapy selection and to evaluate response. For instance, tumor blood flow and glucose metabolism are routinely measured by positron emission tomography (PET) to (1) assess the therapeutic target, (2) identify resistance factors, and (3) measure early response. While neither blood perfusion nor glucose metabolic rate of locally advanced breast cancer can be positively correlated with any diagnostic value; the ratio of blood perfusion over metabolism serves as a good indicator for prognosis. This clearly demonstrates the importance to measure both parameters simultaneously. Furthermore, now blood perfusion can be measured by MRgHIFU and the metabolic rate can be measured by magnetic resonance spectroscopy, therefore, these TSLIP-MRgHIFU systems and methods can perform similar function as PET for guided cancer therapy. However, there are distinct advantages of MRgHIFU-TSLIP over PET. Firstly, MRgHIFU is completely non-invasive and can be performed repeatedly as needed. Second, as compared to PET, MRgHIFU is fast, easy to set up and much less expensive. Lastly, unlike PET, MRgHIFU does not require the use of radioactive tracer material required.

Furthermore, since increased blood flow will increase the amount of drugs passing through the heated tumor per unit time and both elevated temperature and mechanical vibration are expected to enhance the therapeutic drug effect, TSLIP-MRgHIFU mediated therapy may be used for targeted drug delivery of chemotherapeutic drugs. Further, TSLIP-MRgHIFU mediated therapy may also be combined with magnetic resonance spectroscopy to evaluate the drug effect. Controlled increase of blood perfusion at a specific target other than cancer can strategically facilitate the drug delivery in general. Therefore MRgHIFU-TSLIP is not only a diagnostic tool, but also a powerful tool for the enhancement of therapeutic effects of a drug via targeted drug delivery. In an embodiment of the present disclosure, the local blood perfusion rate in the target tissue, during MRgHIFU ablation may be measured using the temperature profile. In some embodiments, the local blood perfusion rate in the target tissue may be measured by injecting a contrast agent so that the local perfusion can be directly imaged by the MR scanner.

ADDITIONAL EMBODIMENTS

Reference will now be made to various embodiments of the present disclosure and experimental results that provide support for such embodiments. However, Applicants note that the disclosure herein is for illustrative purposes only and is not intended to limit the scope of the claimed subject matter in any way.

EXAMPLES

Prior methods have described MRI-based methods for estimating tissue thermal conductivity. However, these approaches involve only modest heating of tissues (up to 15° C. above normal tissue temperature), which is not high enough to induce thermo-coagulative necrosis. In this example, Applicants demonstrate that the thermal conductivity of tissues may be estimated in vivo from MRI-based temperature measurements of tissues treated with high-temperature thermal ablations that cause coagulative necrosis. Compared with other MRI-based methods, such ablations require much higher temperatures, and the tissue thermal property response at these high temperatures is unknown.

The methods discussed herein were devised for estimating the thermal conductivity of tissue in vivo at temperatures between 60° C. and 90° C. The methods disclosed herein allow for the estimation of tissue thermal conductivity in the context of clinical thermal ablation using magnetic resonance-guided high-intensity focused ultrasound (MRgHIFU) surgery. The methods disclosed herein also allow one to reproducibly determine thermal conductivity in pig thighs treated with high-intensity focused ultrasound (HIFU) at therapeutic levels (100 to 140 W) over a relatively short period (10 to 70 seconds). Exemplary approaches for the measurement of thermal conductivity are described herein.

Example 1

Non-Invasive Estimation of Tissue Thermal Conductivity from Spatio-Temporal Temperature Profiles of Volumetric Sonications Using Magnetic Resonance Imaging Guided High Intensity Focused Ultrasound (MR-HIFU) Therapy Animal Protocol The study was performed at two Institutions, and the protocol for this study was approved by respective Institutional Animal Care and Use Committees. A total of 4 healthy pigs (body weight, 50 to 65 kg) were enrolled in the study. Three of the pigs were treated at one institution, and another animal was treated at another institution. Both facilities used the same experimental procedures and the same hardware and software configurations.

Using a clinical MRgHIFU surgical technique, Applicants created thermal lesions in both hindthigh muscles of the 4 pigs. To facilitate propagation of the HIFU beam through the skin, each hind leg was shaved and any remaining hair was removed with hair-removal cream. Each pig was sedated by injecting telazol (4 to 6 mg/kg) and atropine sulfate (0.02 to 0.05 mg/kg) intramuscularly. The animal was then moved into the MRI scanner (1.5 T Achieva; Philips Healthcare, Best, The Netherlands) and was placed in either the right or left decubitus position on top of the HIFU device, which was integrated into the MRI scanner's table top. To avoid unwanted motion during HIFU sonication, the pig was further sedated throughout the procedure by means of a propofol drip (180 mL/hour). The animal's body temperature and cardiac frequency were monitored with a rectal temperature probe and vectorcardiography, respectively. At the end of the MRgHIFU session, the pig, which was under deep anesthesia, was euthanized with an intravenous injection of a lethal dose of potassium chloride (60 to 90 mEq), per institutional guidelines.

MRgHIFU Experimental Setup

Figure 2:
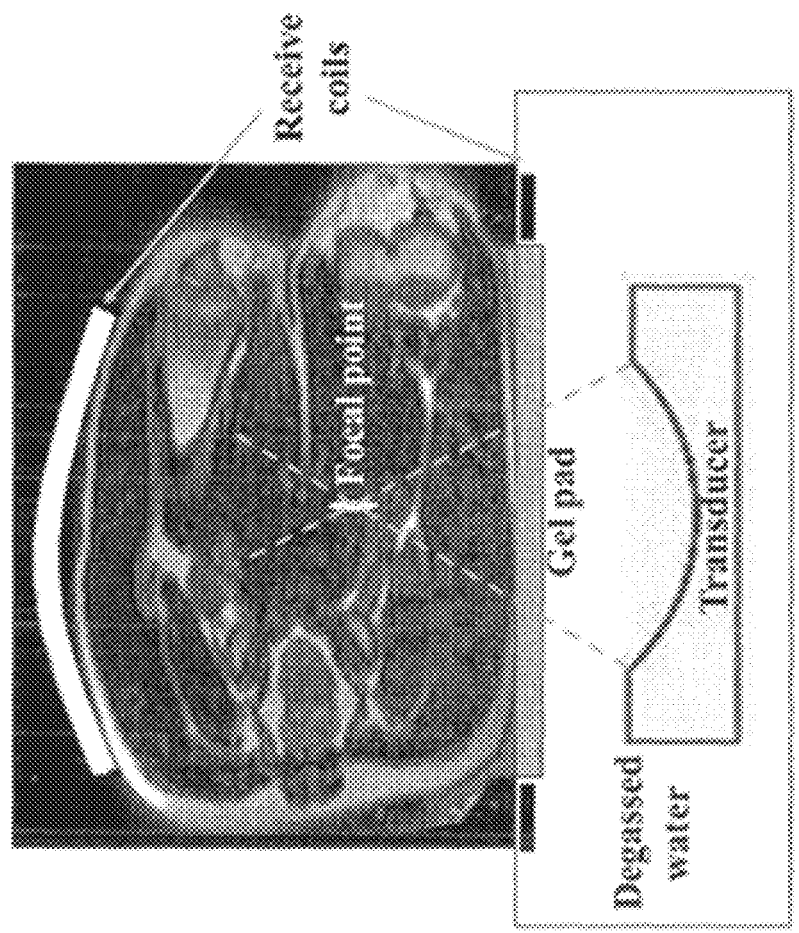
FIG. 2. is a schematic representing the positioning of the target tissue in a commercially available clinical Magnetic Resonance guided High Intensity focused ultrasound (MRgHIFU) platform. In many Magnetic Resonance guided Focused Ultrasound Surgery (MRgFUS) platforms, the transducer, and the signal receiving RF coils are embedded as part of the table top in a Magnetic Resonance Imaging (MRI) scanner.

All HIFU sonications performed in this study were optimized for MRgHIFU surgery and were implemented on a HIFU system integrated with a clinical 1.5T MRI scanner (Sonalleve™, Philips Healthcare, Finland). The system consists of a 256-element spherical-shell, phased-array transducer (Imasonic SA, Besanyon, France) with a 12-cm radius of curvature, 13-cm aperture, radiofrequency generator cabinet, workstation for therapy control, and integrated 3-element MRI receiver coil suitable for imaging. One of the coil elements was located around the acoustic window in the table top, and the other 2 coil elements were immersed in a freely movable, curved, rigid plastic container that was strapped on top of the animal. The ultrasound propagated out of the water bath and through an acoustic window in the HIFU table top. Acoustic coupling with the pig was ensured by placing a gel pad between the window and the pig's leg. A mixture of ultrasound transmission gel and degassed water was added to both sides of the gel pad to further improve coupling at the interfaces (FIG. 2).

Using this volumetric ablation stratagem and either a feedback or a non feedback algorithm, the ultrasound treatments were performed at 1.2 and 1.4 MHz. The intrinsic focus of the ultrasound transducer was an ellipsoid with the dimensions of 1×1×7 mm³. Volumetric ablation was achieved by electronically steering the focus along pre-defined trajectories (consisting of multiple outward-moving concentric circles and subtrajectories with diameters of 4 mm, 8 mm, 12 mm, or 16 mm) positioned in the plane perpendicular to the ultrasound propagation beam and centered on the axis of propagation. The sonication volume encompassed by the predefined trajectory is referred to as a cell, e.g., volume encompassed by a 4 mm trajectory is referred to as a 4 mm cell. The feedback control algorithm then regulated the treatment by controlling the duration of sonication for each subtrajectory; to determine whether to continue sonicating at the current subtrajectory or switch to the next, the temperature and/or thermal dose information was used at the target volume for each dynamic image-set. With the non-feedback control treatment, the duration of sonication for each subtrajectory was fixed.

Magnetic Resonance Imaging Thermometry

Figure 3:
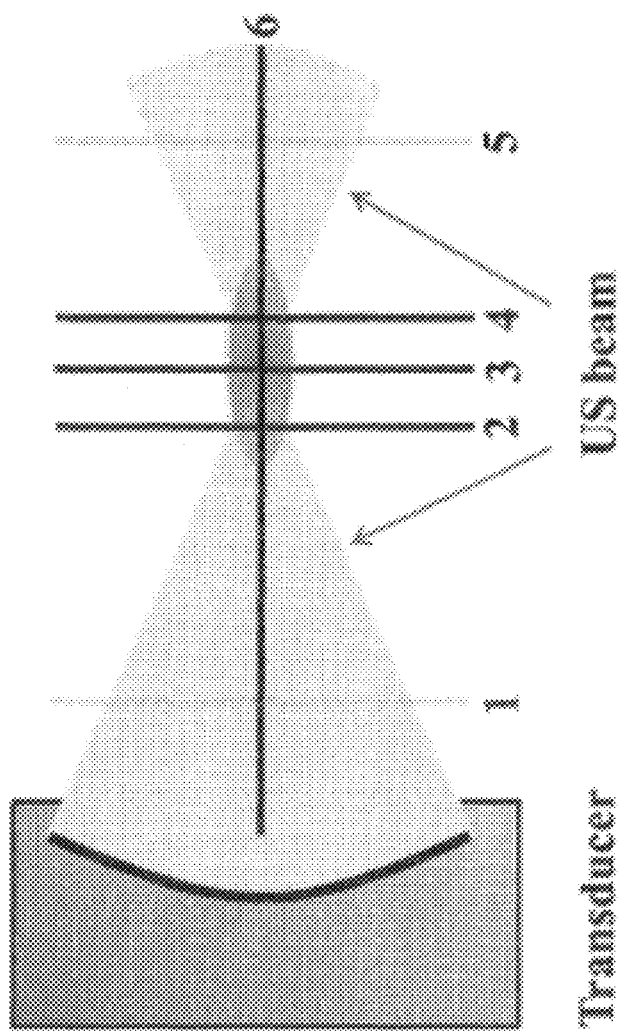
FIG. 3. depicts relative positions of the slices of tissue (in this instance six) used for real-time monitoring of temperature elevation. The real-time temperature profile information thus obtained is passed to the ultrasound controller as well as the decision logic program for administering the active agent(s)

The optimized magnetic resonance temperature imaging (MRTI) sequence for clinical MRgHIFU surgery was as follows. Multi-plane temperature images were acquired in real time during HIFU sonications using a multi-shot echo-planar imaging (EPI) technique with the following acquisition parameters: repetition time (TR)=37 ms; echo time (TE)=20 ms; flip angle (FA)=20°; voxel size=2.5×2.5×7 mm³; matrix size=160×99; field of view (FOV)=400×248 mm; EPI factor=11; and a 1-2-1-binomial water selective excitation pulse. A total of 6 7-mm slices were used to monitor temperature elevation during sonication (FIG. 3). Three of the five coronal slices with a 0-mm inter-slice gap, stacked in the coronal plane perpendicular to the ultrasound beam axis, automatically bisected the focal ellipsoid (one slice was displaced at the center of the ellipsoid). One sagittal slice (parallel to the ultrasound beam axis) was also automatically positioned to allow visualization of the long axis of the ellipsoid crossing the center of the sonicated volume. The two remaining coronal slices were placed in the near field close to the skin and in the far field to monitor for any unintended temperature elevation near critical structures outside the intended ablation zone. The total acquisition time for all six slices was 2.9 seconds per dynamic acquisition. The standard deviation of the phase measurement ($\sigma_T$) is inversely related to the signal-to-noise ratio (SNR) of the MR magnitude image as follows:

$$SNR = \frac{1}{\alpha \gamma TEB_0} \frac{1}{\sigma_T} \quad (1)$$

where $\gamma$ is the gyromagnetic ratio, $B_0$ is the main magnetic field, and TE is the echo time. Temperature information was overlaid only on those pixels with a $\sigma_T$ of <3° C. (SNR masks). Being devoid of distracting pixels (e.g., air space outside the anatomy of interest), such SNR-masked temperature images facilitated the visualization of temperature data. Furthermore, baseline drift in temperature maps was corrected by measuring the average temperature changes in pixels that were outside the focal-spot radius (30 mm) and that had a $\sigma_T$ of <3° C.

Theoretical Background for Extracting Thermal Conductivity

The bio-heat transfer model describes the spatio-temporal temperature evolution in tissue in the absence of large-vessel flow according to the following equation:

$$\rho_t c_t \frac{\partial T(\vec{r}, t)}{\partial t} = k_t \nabla^2 T(\vec{r}, t) - \rho_b \omega_b c_b (T(\vec{r}, t) - T_a) + Q \quad (2)$$

where $T(\vec{r},t)$ is the tissue temperature at time t and location $\vec{r}$, $\rho_t$, $c_t$, and $k_t$ are tissue density, specific heat, and thermal conductivity, respectively; $\rho_b$, $c_b$, $\omega_b$, and are blood density, specific heat, and perfusion respectively; $T_a$ is the arterial blood temperature; and Q is the external total power deposition per unit volume. Considering an equal density and specific heat of tissue and blood ($\rho=\rho_b$, $c_t=c_b$), an averaged constant thermal conductivity of the tissue, and only the cooling period (Q=0), equation (2) can be rewritten in a simpler form:

$$\frac{\partial T(\vec{r}, t)}{\partial t} = D\nabla^2 T(\vec{r}, t) - \omega_b T(\vec{r}, t) \quad (3)$$

where $$D = \frac{k_i}{\rho_i c_i}$$

is the thermal diffusivity in [m²s⁻¹]. This could be analytically solved using Fourier transformation over spatial coordinates:

$$\frac{\partial T(\vec{k}, t)}{\partial t} = -(k^2 D + \omega_b) T(\vec{k}, t) \quad (4)$$

where $T(\vec{k},t)$ is the spatial Fourier transformation of $T(\vec{r},t)$. The analytical solution for this 1st-order differential equation during the cooling period is $$T(\vec{k},t)=T(\vec{k},0)\exp(-k^2 Dt)\cdot\exp(-\omega_b t) \quad (5)$$

where $T(\vec{k},0)$ is the initial spatial temperature distribution at the beginning of the cooling period in the Fourier domain. The spatial distribution of the HIFU beam energy deposition is approximated by a 3-dimensional (3D) Gaussian distribution that has longitudinal and transverse dimensions with respect to the ultrasound beam direction and that depends on ultrasound frequency, the radius of curvature, and the aperture of the transducer. Although the Gaussian fitted spatial distribution of temperature is ideally suited for a fixed-focal-point heating strategy, the initial spatial temperature distribution $T(\vec{k},0)$ right after heating could still be fitted as a Gaussian function in the volumetric heating strategy during the cooling period. The Gaussian temperature distribution in the spatial domain results in the following expression in the Fourier domain:

$$T(\vec{k}, 0) = T_0 (2\pi)^{\frac{3}{2}} \sigma_{0xy}^2 \sigma_{0z} \exp\left[-\frac{(k_x^2 + k_y^2)\sigma_{0xy}^2}{2}\right] \exp\left[-\frac{k_z^2 \sigma_{0z}^2}{2}\right] \exp[-w_b t] \quad (6)$$

where $T_0$ is the temperature at the trajectory center at the end of the sonicating period and where $\sigma_{0xy}$ and $\sigma_{0z}$ are the Gaussian variances (temperature spatial spread) in the horizontal (Oxy) and vertical (Oz) directions, respectively. The analytical solution of spatial temperature evolution is solved by inserting equation (6) into equation (5) through the inverse Fourier transform:

$$T(\vec{r}, t) = T_0 \frac{\sigma_{0xy}^2}{\sigma_{0xy}^2 + 2Dt} \sqrt{\frac{\sigma_{0z}^2}{\sigma_{0z}^2 + 2Dt}}$$
$$\exp[-w_b t]\exp\left[-\frac{x^2 + y^2}{2\sigma_{0xy}^2 + 4Dt}\right]\exp\left[-\frac{z^2}{2\sigma_{0z}^2 + 4Dt}\right] \quad (7)$$

Note that the perfusion term in equation (7) serves as a scaling factor, while diffusivity is the only factor that governs the shape of the Gaussian temperature spread and the rate with which the Gaussian expands:

$$\frac{\partial(\sigma_{xy}^2)}{\partial t}.$$

So, in this case, the dependency of Gaussian variance on thermal diffusivity can be calculated from the temperature evolution from the coronal slices as follows:

$$m = \frac{\partial(\sigma_{xy}^2)}{\partial t} = \frac{\partial(2\sigma_{0xy}^2 + 4Dt)}{\partial t} = 4D = \frac{4k_t}{\rho_t c_t} \quad (8)$$

where m is the slope of the Gaussian variance change in the time domain and where $\rho_t$ (1060 kg/m$^3$) and $c_t$ (3600 J/kg*K) are the tissue density and specific heat, respectively. The perfusion term in equation (7) will not affect the change in Gaussian variance but will affect only the peak value of the Gaussian temperature spread. Hence, thermal conductivity could be estimated by exclusively analyzing the change in Gaussian variance of the temperature spread in equation (8) and is independent of blood perfusion.

Post Processing of Temperature Profiles to Extract Thermal Conductivity

To estimate thermal diffusivity, Applicants analyzed the evolution of the spatial spread of temperature maps during the cooling period. Post-processing of the temperature-drift corrected-phase data involved two steps. First, the temperature distribution on each of the 3 coronal planes (in a 75×75 mm$^2$ region located around the center of HIFU cell trajectories) at each of the cooling time points, was fitted by a 2-dimensional (2D) Gaussian function based on equation (7) by using a Levenberg-Marquardt algorithm and custom software in MATLAB (Math Works Inc., Natick, Mass., USA) to determine Gaussian variance $\sigma^2_{xy}(t)$. However, under clinical surgical conditions, only a subset of fitted Gaussian variances was useful for the linear fitting of thermal conductivity. The selected subsets were those in which the r$^2$ of the goodness of fit of 2D Gaussian variance was >0.85. To improve the quality of fit, each temperature value included in the 2D fit was weighted by the magnitude of the corresponding voxel, as the phase standard deviation is known to be inversely proportional to the SNR of the complex MR image. The fit yielded the Gaussian variance of the temperature spread $\sigma^2_{xy}(t)$ at each time point.

Second, the temporal evolution of Gaussian variance $\sigma^2_{xy}(t)$ was fitted to a linear function of cooling time. The local tissue thermal diffusivity D was the slope of the fit, and thermal conductivity $k_t$ was then calculated according to equation (8). The thermal conductivity value corresponding to the fit that yielded the highest r$^2$ value (r$^2$>0.9) among the coronal slices was chosen as the estimated thermal conductivity.

Results

Applicants performed a total of 40 volumetric ablations in the thigh muscles of 4 pigs by using a clinical MRgHIFU surgery procedure with either a feedback (n=25) or a non-feedback (n=15) algorithm (Table 1). Thirty-five of the attempted ablations were successfully completed. Twenty-three of these procedures used a feedback algorithm, and the other Twelve used a non-feedback algorithm. In 3 out of the 5 unsuccessful cases, the safety algorithm caused the treatments to be automatically discontinued once the near-field or far-field temperature exceeded the predefined temperature safety limit; in the other 2 cases, treatment failure was due to equipment malfunction. The mean standard deviation for the temperature in untreated regions was 1.1±0.2° C. Real-time temperature maps for all treatment cell sizes (4, 8, 12, and 16 mm) were ellipsoidal, the longest axis, as expected, being in the direction of propagation of the HIFU beam (as seen in the sagittal monitoring plane and in a circular cross-section in each of the 3 coronal treatment planes).

TABLE 1

Summary of Experiments Performed in Each Pig

| Pig | Body Temp (° C.) | No. of Sonications | Maximum Temperature (° C.) | Power (W) | Duration (sec) |
|---|---|---|---|---|---|
| 1 | 36 | 4 | 65.4-71.6 | 140 | 20.8-70.7 |
| 2 | 36 | 2 | 65.1-65.6 | 140 | 27.7 |
| 3 | 35.5 | 4 | 67.1-86.3 | 140 | 24.4-65.1 |
| 4 | 34.8 | 25 | 57.7-79.7 | 100~130 | 20.1-76.4 |

Figure 4:
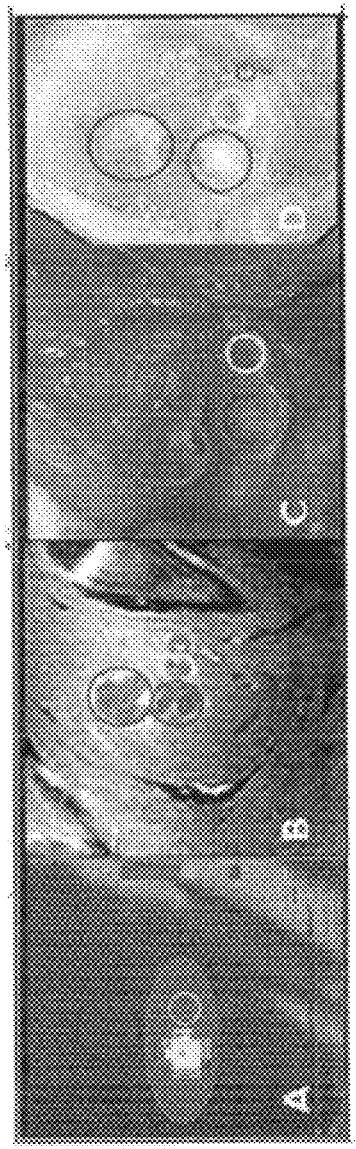
FIGS. 4A-4D. show a typical example of the use of imaging at various stages in the TSLIP-MRgHIFU set up. Previously acquired Magnetic Resonance (MR) images of the region of interest are displayed on the treatment planning console (FIG. 4A); Ellipsoidal regions, to which the ultrasound energy may be focused within the tissue, are specified by the operator on the images. The ellipsoidal regions, referred to as cells, may be of different sizes with circular cross-sectional diameters ranging from 4-mm (green circles), 8-mm (yellow circles), 12-mm (pink circles), and 16-mm (red circles) (FIG. 4A). During heating or thermal stimulation, a real-time temperature/thermal dose map is overlaid on the anatomic images. A representative overlay is shown on the 12-mm cell[s]. The effectiveness of therapy may be monitored by acquiring images after treatment with administration of the MR contrast agent. Such images may reflect treated regions as volumes devoid of perfusion (FIG. 4B). The effectiveness of the therapy may also be confirmed with necropsies performed immediately after treatment (FIG. 4C), or after necropsy and immersion in formalin (FIG. 4D), showing well-formed clearly circumscribed lesions.

FIG. 4A-4D presents the complete sequence of steps, including imaging on the planning console before sonication (FIG. 4A), MR evaluation of the nonperfused lesion (FIG. 4B), and pathologic evaluation (FIG. 4C, 4D). At each step, the results showed excellent correspondence to one another.

Figure 5A:
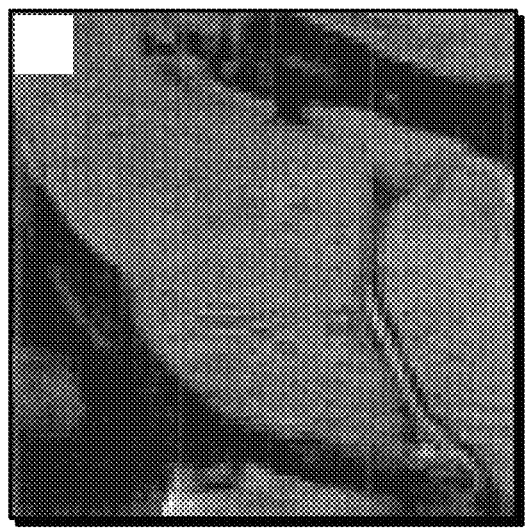
FIGS. 5A-5F. depict results of a typical high-intensity focused ultrasound sonication using magnetic resonance (MR) thermometry. Magnetic resonance (MR) image showing the anatomy of the pig leg (FIG. 5A). Color-coded temperature distribution overlaid on the MR anatomic information (FIG. 5B). Temperature evolution at the trajectory center (black arrow in view B) and the region outside of the heating (blue arrow in view B) (FIG. 5C). Time point $t_c$ corresponds to the point at which the ultrasound was discontinued (FIG. 5D). Experimental temperature spread (circle) and the associated 2D Gaussian fit of the temperature profile right at different time points after sonication is shown in FIG. 5E. Gaussian fitted temperature profiles across 23 the trajectory center for 3 different time points during the cooling period is shown in FIG. 5E and this spread may be used to estimate local tissue thermal conductivity (FIG. 5F) (Zhang et al., JMRI, 2012).
Figure 5B:
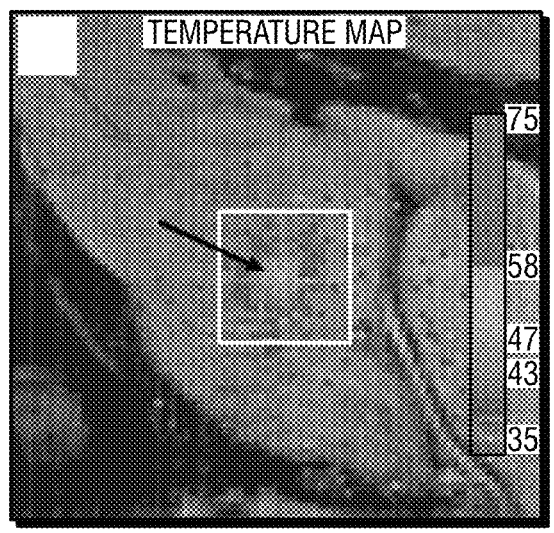
Figure 5C:
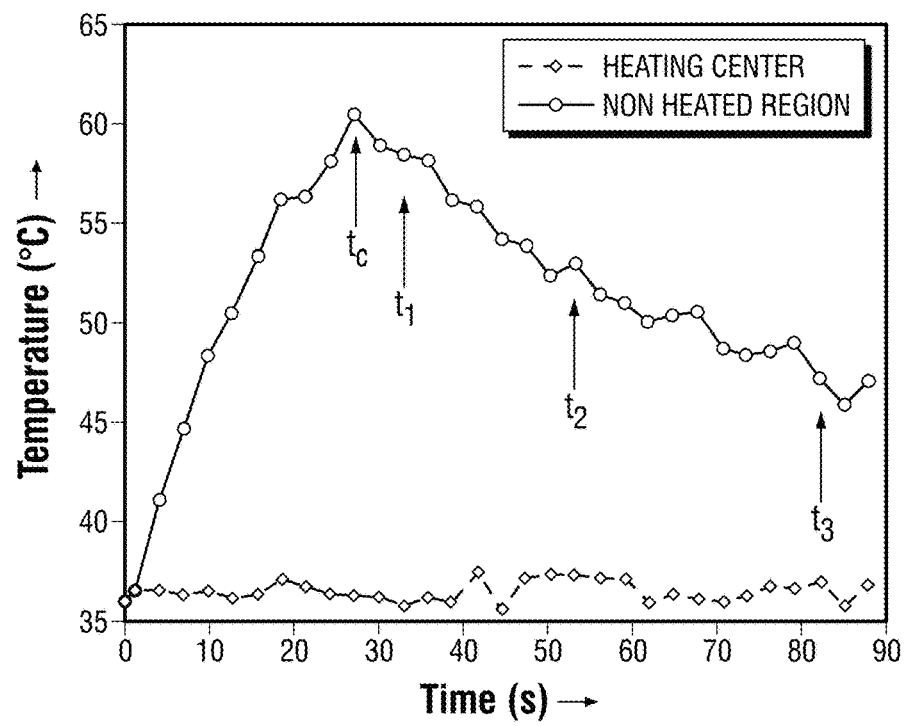
Figure 5D:
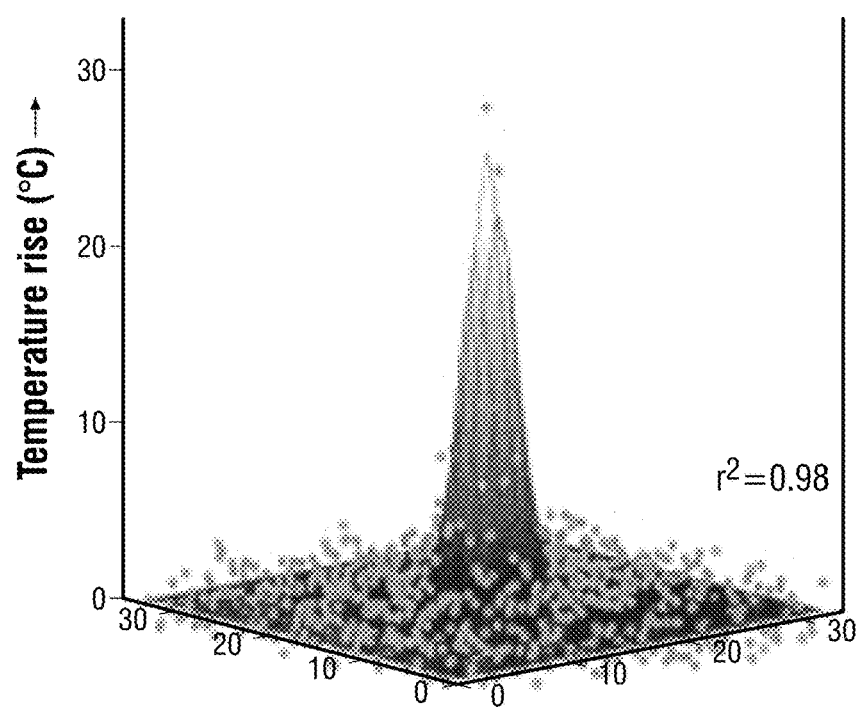
Figure 5E:
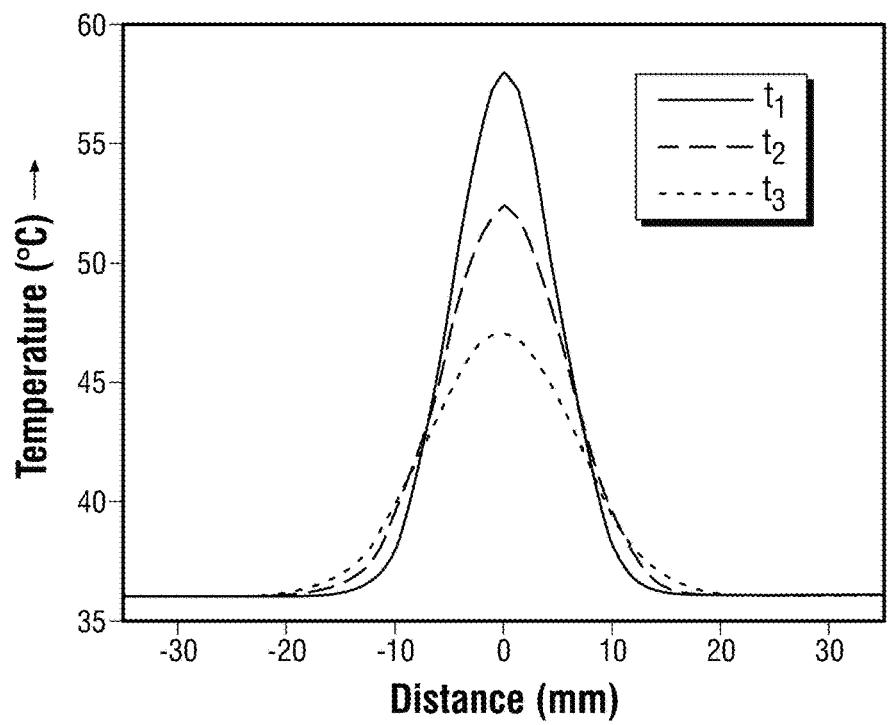
Figure 5F:
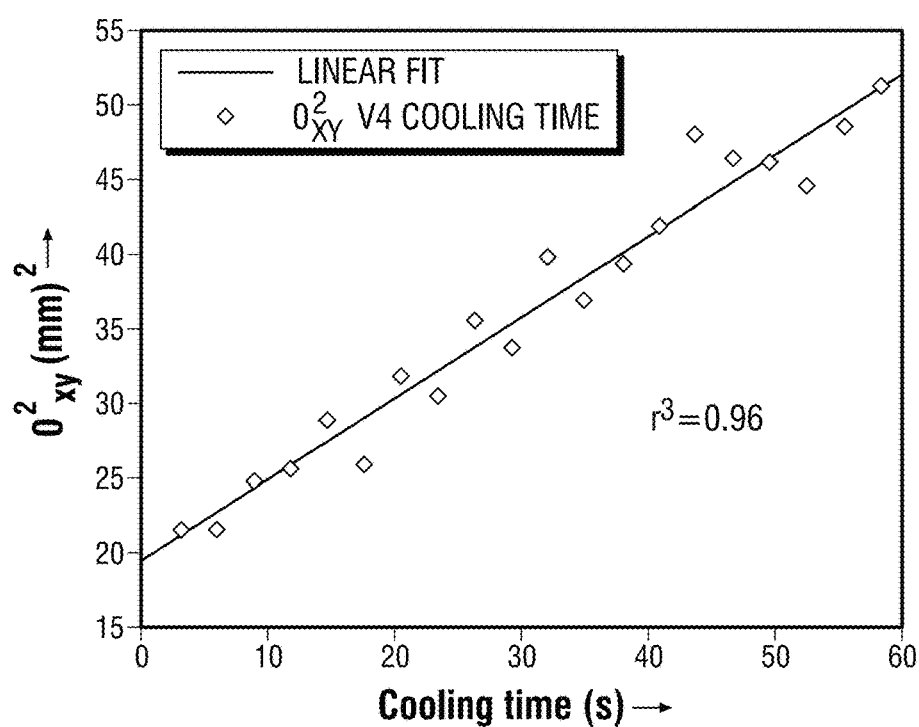

FIG. 5A-5F shows the results of a representative HIFU nonfeedback sonication of an 8-mm treatment cell. FIG. 5A clarifies the anatomic structure of the pig leg, and FIG. 5B shows a temperature map in the coronal plane at the end of HIFU treatment; the arrows indicate the location of the heating center (black arrow) and a representative voxel outside the heated region (blue arrow). The temporal evolution of these 2 points is plotted in FIG. 5C. The standard deviation of the temperature (1.1±0.2° C.) confirms the precision of the MRI thermometry. The temperature increased during HIFU sonication and then decreased after sonication (FIG. 5C) as a result of heat conduction and convection, which are influenced by tissue conductivity, blood perfusion, and the external heat source. FIG. 5D displays the spatial spread of the temperature map and the quality of the 2D Gaussian fit right after heating. FIG. 5E shows Gaussian-fitted temperature profiles around the trajectory center at 32.8 (t$_1$), 50.2 (t$_2$), and 82.2 seconds (t$_3$)

after HIFU sonication was discontinued. The temporal evolution of Gaussian variance $\sigma^2_{xy}(t)$ and the associated linear fit are shown in FIG. 5F. This graph indicates a linear regression in time with goodness of fit ($r^2$=0.96). The average thermal conductivity based on equation (8) is 0.51 W/(m*K) and 0.54 W/(m*K) from institution 1 and institution 2, respectively, with a reproducibility of 10% in both cases (FIG. 5A,B).

Equipment and Facilities

The majority of focused ultrasound systems have one big ultrasonic disc and the focal point is adjusted by mechanically moving of the disc. For the PHILIPS HIFU system both the power and the phase of each transducer element are independently programmable which provides the ability to heat a volume of the tissue by dynamically moving the focal point of the ultrasound beam. The treatment may discontinue once the target thermal dose or temperature is reached through monitoring the temperature elevation in real-time. The clinical optimized volumetric ablation has significantly increased the treated volume.

Figure 6:
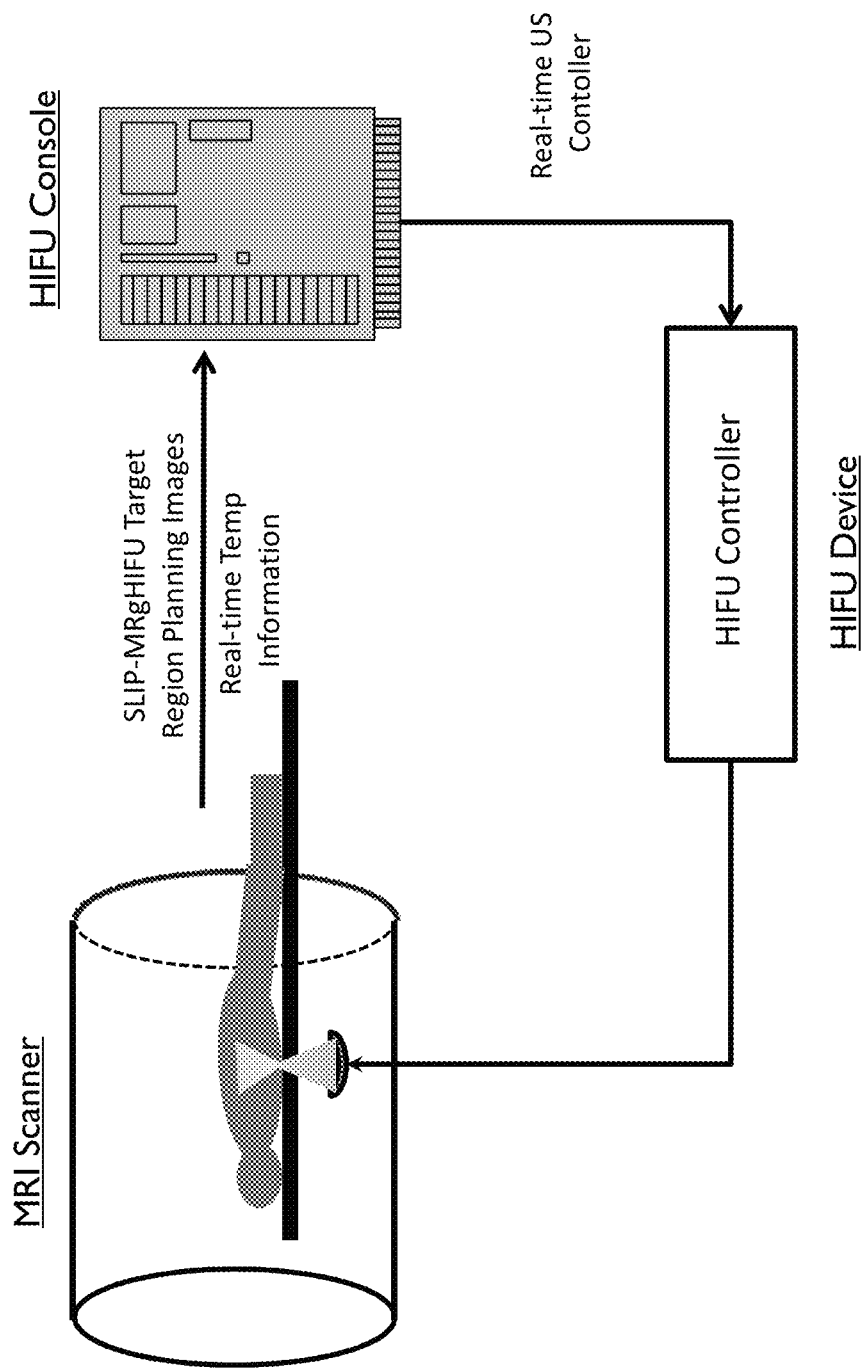
FIG. 6 is an illustrative implementation of an MR with integrated HIFU.

FIG. 6 is a HIFU therapy system integrated into a MR scanner. The 3D anatomic images acquired by the scanner can be sent to HIFU therapy console. Then one can define the location of target and the therapy plan on the therapy console. During the sonication, the scanner measures and provides the real time feedback of the temperature for the therapy console to control the transducer to carry out MRgHIFU surgery according the pre-defined therapy plan.

Example 2

Temperature Dependent Perfusion Rate Model

In this example, Applicants report that a fast temperature-dependent perfusion rate is necessary to account for the time evolution of the temperature of the entire HIFU treatment. Further, Applicants report that (i) Temperature dependent perfusion rate is needed to properly describe the local physiologic response of tissue to HIFU treatment; (ii) Local blood perfusion rate responses are much faster than that have been reported in hyperthermia treatment; (iii) Fast blood perfusion increases with increasing local temperature should be considered in clinical HIFU therapy planning and optimization.

Animal Care

The study was approved by the Institutional Animal Care and Use Committee (IACUC). The animals were sedated throughout the volumetric MRgHIFU procedure, and sacrificed immediately thereafter under institutional guidelines. Thermal ablation of thigh muscles were performed in five pigs (50-65 kg).

MR-HIFU Procedure

All ablations were done on a Philips 1.5T MR scanner (Achieva) with a 256Ch spherical shell HIFU transducer (frequency range 1.2-1.4 MHz), and an integrated receiver coil. The spatio-temporal temperature evolution in volumetric sonication was recorded in real-time using a multi-shot echo planar imaging technique (EPI).

Simulation of Blood Perfusion Rate Response

The spatio-temporal temperature evolution of HIFU treatment was modeled using bio-heat transfer equation (Pennes H H J. Appl. Physiol. 1:93, pp 1948). This equation was simplified by Goldberg et al., to the following: coagulation necrosis equals energy deposited multiplied by local tissue interactions minus heat loss. Three models were used for simulation in which: 1) both the thermal conductivity and perfusion rate were constant; or 2) thermal conductivity was assumed to be a linear function of temperature and blood perfusion rate was fixed at normal perfusion rate for muscle (6.71×10-4 s-1); or 3) the blood perfusion rate was assumed to be a temperature dependent parameter. Blood perfusion rate linearly increased from normal perfusion rate with the temperature rise followed by a more rapid linear decay with the temperature decrease (FIG. 7A). The evolution of blood perfusion rate versus time was shown in FIG. 7A. All simulations were performed in MATLAB™ (MathWorks Inc., MA, USA) and Comsol 3.5a (COMSOL, Inc., MA, USA).

Results

Nine ellipsoidal cells with diameter of 8 mm, 12 mm, 16 mm were successfully treated at different depths (3.7 cm-5.4 cm) on the thigh muscle. The thermal conductivity of 0.54±0.05 W/(m*K) used in model 1 and 3 were extracted from the spatio-temporal temperature distribution of treated pigs muscle using the method described previously (Zhang J. et al., $2^{nd}$ MRgFUS symposium 2010). Perfusion rates previously reported, in models 1 and 2, were 6.71×10-4 s-1 for normal muscle tissue. Specific heat, tissue density of both muscle and blood, and blood temperature in all three models were 3600 J/(kg*K), 1060 kg/m3, and 37° C. respectively. The acoustic power input for each model was estimated based on the peak temperature measured experimentally (86.5° C.), and was 3.25×106 W/m³, 3.46×106 W/m³, and 4.52×106 W/m³ for models 1 through 3 respectively.

Temperature evolution at the center of a 16 mm cell simulated using model 1 through 3 is shown in FIG. 7 (See 7B through 7C), respectively. Sonication duration was 65 s followed by equal amount of time for cooling. The simulation based on the 1st model of constant thermal conductivity and perfusion rate cannot describe the temperature evolution both before and after sonication (FIG. 7B). While model 2 appears to match experimental observation, the thermal conductivity needed to be increased up to 1.2 W/(m*K), which is well beyond the thermal conductivity for soft tissue. In contrast, model 3 (FIG. 7D) matched the experimental data both in heating and cooling period. The perfusion rate went up to 20 times of that of the normal perfusion rate which is similar to that observed in the hyperthermia treatments. However, it should be noted that, unlike hyperthermia where the tissue response time is on the order of tens of minutes, the time scale of tissue response for HIFU treatment is on the order of tens of seconds. The third model also has the ideal characteristic that the perfusion rate decreases faster during the cooling period than the rising period due to the lesion created after sonication.

Example 3

Feasibility of Non-Invasive Measurement of Tissue Thermal Conductivity In Vivo

MR-HIFU is clinically used for non-invasive thermal ablation of tumor tissue based on the absorption of focused ultrasound energy in the target region. The responses of perfusion rate and tissue thermal properties to local heating determine the temperature distribution during sonication and thus affect the effectiveness of the treatment. While it is well known that both the tissue thermal conductivity and the blood perfusion rate increase under hyperthermia treatments (<45° C.), their behaviors in the small focused volume under extreme temperature (>60° C.) conditions prevalent during HIFU surgery are largely unknown. In this example, Applicants simulate the spatio-temporal temperature distribution of pig muscle tissue treated by MR guided HIFU in vivo using three models with various assumptions about tissue thermal conductivity and perfusion rate.

In this example, Applicants report the feasibility of non-invasive measurement of thermal conductivity of muscle in vivo using MR-HIFU ablations.

Animal Care

The study was approved by the Institutional Animal Care and Use Committee. The animals were sedated during the procedure, and sacrificed immediately thereafter under Institutional guidelines.

MR-HIFU Procedure

All experiments were done on a Philips 1.5T MR scanner (Achieva) with a 256Ch spherical shell HIFU transducer (frequency range 1.2-1.4 MHz), and an integrated receiver coil. The temperature evolution after volumetric sonication (n=10) was recorded in real-time using a multi-shot echo planar imaging technique [A3]. Three slices (at xy plane) bisected the focal ellipsoid coronally, and one sagittal (at z plane) slice was positioned to visualize the long axis of the ellipsoid.

Estimation of Thermal Conductivity:

The spatio-temporal temperature evolution following heating is modeled by a Gaussian distribution and thermal conductivity is calculated based on BHT model [2]. In Equations (7) and (8) (see the present disclosure at paragraphs 0082 and 0084, respectively), $\tau_{o\,xy}$ and $\tau_{oz}$ represent the standard deviation of the spatio-temporal spread modeled as a Gaussian in the coronal and sagittal planes respectively at the end of sonication, and D represents the thermal diffusivity, and $W_b$ represents the perfusion rate, and $T_o$ represents peak temperature, and $\rho$(1060 kg/m3) and C(3600 J/kg*K) are the tissue density and specific heat respectively. Spatial temperature distribution at a given time on the coronal slice was fitted by a 2D Gaussian (Equation 7) to determine $\sigma^2_{xy}(t)$ using MATLAB™. The rate of change of $\sigma^2_{xy}$ over time yields thermal diffusivity D and thermal conductivity k (Equation 8).

Results 10 cells with diameter of 4 mm, 8 mm, 12 mm, 16 mm were successfully treated at different depths (3.7 cm-5.4 cm) on the thigh muscle of five pigs (50-65 Kg) as described in [A3]. FIG. 5D depicts the spatial temperature distribution over an (75*75 mm$^2$) area centered at the focus of the 8 mm ultrasound cell, right after the heating is stopped (27.72 s). The Gaussian surface fit over the temperature in this area is shown in FIG. 5E. The time course of the Gaussian variance in coronal plane during the cooling period is shown in FIG. 5F. The thermal conductivity for the pig muscle estimated from the ten sonications (0.54±0.05 W/mK) and is consistent with the reported values. Applicants report the feasibility of non-invasive measurement of thermal conductivity of muscle in-vivo using MR-HIFU ablations.

Discussion

Although researchers have proposed several invasive approaches for measuring tissue thermal conductivity in vivo, these methods are limited by an inability to separate the relative contribution of heat conduction and perfusion components. Noninvasive approaches such as MRI do not have this limitation. However, a noninvasive method for accurately determining tissue thermal conductivity during clinical MRgHIFU surgery has not yet been investigated.

In clinical MRgHIFU procedures, safety requirements necessitate that additional slices be obtained to monitor the temperature in the near and far fields of the ultrasound beam and, thus, avoid overheating outside the target region. A larger surface coil is also necessary. These requirements decrease the spatial and temporal resolution and increase the uncertainty of temperature measurements. The methods disclosed herein for MRgHIFU surgery resulted in a temperature uncertainty, spatial resolution, and temporal resolution of 1.1±0.2° C., 2.5×2.5×7 mm$^3$, and 2.9 seconds, respectively.

In an exemplary embodiment of the present disclosure, an in vivo pig model was used to test the feasibility and precision of measuring tissue thermal conductivity in a high temperature range (60° C.<T<90° C.) using data sets obtained from optimal clinical MRgHIFU surgery procedures. High intensity ultrasound focus was steered at predefined trajectory paths (diameter: 4, 8, 12, and 16 mm) to heat pig thigh muscle with feedback or nonfeedback control. Each cell was heated to between 60° C. and 90° C. and then cooled naturally. The duration of heating varied between 20 and 71 seconds, depending on the type of ablation control (feedback or non-feedback) and size of the treatment volume that was ablated. The spatio-temporal temperature data were analyzed by following the same data process used in determining thermal conductivity.

Despite the slightly lower spatial resolution of the MRTI sequence, which was used to meet the clinical imaging requirements, the precision (~10%) of in vivo tissue thermal conductivity estimates was similar to that described in previous reports. The results suggest that thermal conductivity can be measured during clinical MRgHIFU surgery with similar precision as reported previously. Estimation of the absolute thermal conductivity value of muscle is also consistent with the reported values for muscle at temperature of <40° C. [0.52-0.62 W/(m*K)].

Because these animal studies were implemented under conditions similar to those used for clinical surgical procedures, the muscle in the target region was heated to cause necrosis. Our results indicate that the thermal conductivity of muscle tissue, whether living or dead, undergoes very little variation at high temperatures, a behavior that is similar to what has been reported in the literature for temperatures in the range of 28.5~32.6° C.

Using the above-described approach for estimating thermal conductivity, the analysis of temperature evolution during the heating of human uterine fibroid tissue in vivo yielded a thermal conductivity of 0.460±0.03 W/(m*K) (data not shown). These data with in vivo thermal ablation demonstrate that it may be possible to calculate in vivo such bio-heat properties during MRgHIFU surgery in patients.

Another interesting approach for estimating tissue bio-heat properties involves the development of numerical bio-heat transfer models using a finite element approach in which MR temperature images are the initial conditions.

In these examples, Applicants report the feasibility of a noninvasive method to estimate local tissue thermal conductivity in vivo in a range of high temperatures (60° C.<T<90° C.) that would be expected to occur during clinically relevant MRgHIFU. It is estimated that the thermal conductivity of in vivo pig skeletal muscle at these high temperatures is 0.54±0.05 W/(m*K), which is consistent with reported values. Further, Applicants demonstrate that thermal conductivity at high temperatures is similar to thermal conductivity at lower temperatures. These studies provide important information for optimizing the delivery of thermal energy into the target tissue.

In an exemplary embodiment, Applicants have established standard criteria for estimating thermal conductivity using a clinical MRgHIFU procedure, and have successfully applied this method for the treatment of uterine fibroid tissue by means of clinical MRgHIFU (data not shown).

Implementations described herein are included to demonstrate particular aspects of the present disclosure. It should be appreciated by those of skill in the art that the implementations described herein merely represent exemplary implementation of the disclosure. Those of ordinary skill in the art should, in light of the present disclosure, appreciate that many changes can be made in the specific implementations described and still obtain a like or similar result without departing from the spirit and scope of the present disclosure. From the foregoing description, one of ordinary skill in the art can easily ascertain the essential characteristics of this disclosure, and without departing from the spirit and scope thereof, can make various changes and modifications to adapt the disclosure to various usages and conditions. The implementations described hereinabove are meant to be illustrative only and should not be taken as limiting of the scope of the disclosure.

REFERENCES

U.S. Pat. No. 7,981,442
U.S. Pat. No. 7,807,134
U.S. Pat. No. 7,758,541
U.S. Pat. No. 7,505,807
U.S. Pat. No. 7,479,483
Dragonu I et al. NMR in Biomedicine, 22, 843, 2009.
Pennes H H J. Appl. Physiol. 1, 93, 1948.
Zhang J et al. ISMRM, #4131, 2010.
Grossman L, "Reinventing the Inventor", TIME. 2011, November 28, P 74.
Jolesz A. Ference, "MRI-Guided Focused Ultrasound Sugery", Annu. Rev. Med. 2009, 60, P 417-30.
Zhang J, Mougenot C, Partanen A, Muthupillai R and Hor P H, "Volumetric Magnetic Resonance Imaging-Guided High-Intensity Focused Ultrasound for Noninvasive, In Vivo Determination of Tissue Thermal Conductivity: Initial Experience in a Pig Model", A draft of the paper and a one page conference abstract are included in Appendix A.
One animal experiment is depicted in Appendix B.
Zhang J, Hor P H, Fischer J, Pmianen A, Karjalainen T and R. Muthupillai, "A Temperature Dependent Perfusion Rate Model for Simulating Temperature Evolution of Tissue for Magnetic Resonance Imaging guided High Intensity Focused Ultrasound (MR-HIFU) Therapy: Initial Experience in a Pig Model", presented at International Society of Magnetic Resonance in Medicine annual meeting, ISI\IIRM, #1662, Quebec, Canada, May ih_13th, 2011. See abstract in Appendix C.
For a review, see Mankoff D. and Krohn K, "PET imaging of response and resistance to cancer therapy", Cancer Drug Resistance. 2006, P 105-122.
Specht J. et al, "Tumor Metabolisim and Blood Flow as Assessed by Positron Emission Tomorgraph Varies by Tumor Subtype in locally Advanced Breast Cancer", Clinical Cancer Research. 2011, P 2803-2810.
Jansen J F, Backes W H, Nicolay K, Kooi M E, "1H MR spectroscopy of the brain: absolute quantification of metabolites", Radiology. 2006, 240(2), P 318-32.
1. Vanne A, Hynynen K. MRI feedback temperature control for focused ultrasound surgery. Phys Med Biol 2003; 48(1):31-43.
2. Hynynen K. MRI guided focused ultrasound surgery. Med Phys 2002; 29(6):1329-1329.
3. Cline H E, Hynynen K, Hardy C J, Watkins R D, Schenck J F, Jolesz F A. Mr Temperature Mapping of Focused Ultrasound Surgery. Magn Reson Med 1994; 31(6):628-636.
4. Ekstrand V, Wiksell H, Schultz I, Sandstedt B, Rotstein S, Eriksson A. Influence of electrical and thermal properties on RF ablation of breast cancer: is the tumour preferentially heated? Biomed Eng Online 2005; 4:41.
5. Liu Z, Ahmed M, Weinstein Y, Yi M, Mahajan R L, Goldberg S N. Characterization of the RF ablation-induced 'oven effect': The importance of background tissue thermal conductivity on tissue heating. Int J Hyperthermia 2006; 22(4):327-342.
6. Zhu L, Lemons D E, Weinbaum S. A new approach for predicting the enhancement in the effective conductivity of perfused muscle tissue due to hyperthermia. Ann Biomed Eng 1995; 23(1):1-12.
7. Lang J, Erdmann B, Seebass M. Impact of nonlinear heat transfer on temperature control in regional hyperthermia. IEEE Trans Biomed Eng 1999; 46(9):1129-1138.
8. Zhang A L, Xu L X, Sandison G A, Zhang J Y. A microscale model for prediction of breast cancer cell damage during cryosurgery. Cryobiology 2003; 47(2):143-154.
9. Rui J, Tatsutani K N, Dahiya R, Rubinsky B. Effect of thermal variables on human breast cancer in cryosurgery. Breast Cancer Res Tr 1999; 53(2):185-192.
10. Diller K R, Ryan T P. Heat transfer in living systems: Current opportunities. J Heat Transf-Trans ASME 1998; 120(4):810-829.
11. Telenkov S A, Youn J I, Goodman D M, Welch A J, Milner T E. Non-contact measurement of thermal diffusivity in tissue. Phys Med Biol 2001; 46(2):551-558.
12. Anand A, Kaczkowski P J. Noninvasive measurement of local thermal diffusivity using backscattered ultrasound and focused ultrasound heating. Ultrasound Med Biol 2008; 34(9):1449-1464.
13. Cheng H L M, Pewes D B. Tissue thermal conductivity by magnetic resonance thermometry and focused ultrasound heating. J Magn Reson Imaging 2002; 16(5):598-609.
14. Miller N R, Bamber J C, ter Haar G R. Imaging of temperature-induced echo strain: preliminary in vitro study to assess feasibility for guiding focused ultrasound surgery. Ultrasound Med Biol 2004; 30(3):345-356.
15. Dragonu I, de Oliveira P L, Laurent C, et al. Non-invasive determination of tissue thermal parameters from high intensity focused ultrasound treatment monitored by volumetric MRI thermometry. NMR Biomed 2009; 22(8):843-851.
16. Enholm J K, Kohler M O, Quesson B, Mougenot C, Moonen C T W, Sokka S D. Improved Volumetric MR-HIFU Ablation by Robust Binary Feedback Control. IEEE Trans Biomed Eng 2010; 57(1):103-113.
17. Kohler M O, Mougenot C, Quesson B, et al. Volumetric HIFU ablation under 3D guidance of rapid MRI thermometry. Med Phys 2009; 36(8):3521-3535.
18. Salomir R, Palussiere J, Vimeux F C, et al. Local hyperthermia with MR-guided focused ultrasound: spiral trajectory of the focal point optimized for temperature uniformity in the target region. J Magn Reson Imaging 2000; 12(4):571-583.
19. EI-Sharkawy A M, Schar M, Bottomley P A, Atalar E. Monitoring and correcting spatio-temporal
C1. Chang W. Song, IEEE transaction on biomedical engineering, 31(1), 9-16, 1984.
C2. Zhang J et al. ISMRM, #4131, 2010.

C3. Pennes H H J. Appl. Physiol. 1, 93, 1948.
C4. Zhang J et al. 2nd MRgFUS symposium 2010, P21.

What is claimed is:

1. A method of treating a tumor in a subject in need thereof comprising:
   positioning a Magnetic Resonance guided high intensity focused ultrasound transducer to target the tumor;
   energizing the Magnetic Resonance guided high intensity focused ultrasound transducer to thermally stimulate the tumor;
   utilizing a Magnetic Resonance guided high intensity focused ultrasound system to monitor the spatial and temporal temperature distribution of the tumor,
      wherein the monitoring comprises acquiring magnetic resonance thermometry images of the tumor, and
      wherein the magnetic resonance thermometry images of the tumor provide the spatial and temporal temperature distribution of the tumor;
   extracting thermal conductivity as a function of temperature for controlled increase of blood perfusion from a measured spatial and temporal temperature distribution of the tumor during and after thermal stimulation;
   extracting a temperature dependent perfusion rate from the spatial and temporal temperature distribution of the tumor during and after thermal stimulation, wherein the extraction of temperature dependent perfusion rate is based, at least in part, on the thermal conductivity;
   administering a therapeutic agent to the subject;
   providing a controlled thermal stimulation to the tumor,
      wherein the controlled thermal stimulation is provided by the Magnetic Resonance guided high intensity focused ultrasound transducer while monitoring the spatial and temporal temperature distribution of the tumor,
      wherein the controlled thermal stimulation results in a temperature dependent control of blood perfusion rate to the tumor, thereby resulting in a temperature dependent controlled increase of blood perfusion to the tumor, and
      wherein the controlled increase of blood perfusion results in accumulation of the therapeutic agent in the tumor; and
   discontinuing delivery of ultrasound energy when the monitored temperature of the tumor achieves a pre-determined set temperature or temperature profile.

2. The method of claim 1, wherein the therapeutic agent is a chemotherapeutic drug.

3. The method of claim 1, wherein the therapeutic agent is activated by mechanical vibrations.

4. The method of claim 1, wherein the administration of the therapeutic agent occurs simultaneously with the controlled thermal stimulation of the tumor.

5. The method of claim 1, wherein the step of providing the controlled thermal stimulation results in ablation of the tumor tissue.

6. The method of claim 1, wherein the tumor is selected from a group consisting of prostate carcinoma, breast carcinoma, hepatocellular carcinoma, renal cell carcinoma, urinary bladder carcinoma, pancreas cancer, and osteosarcoma.

7. The method of claim 1, the controlled thermal stimulation is performed for a predetermined duration.

8. A method for increasing the efficacy of a therapeutic agent in a target tissue, in a subject in need thereof, comprising:
   positioning a Magnetic Resonance guided high intensity focused ultrasound transducer to target the target tissue;
   energizing the Magnetic Resonance guided high intensity focused ultrasound transducer to thermally stimulate the target tissue;
   utilizing a Magnetic Resonance guided high intensity focused ultrasound system to monitor the spatial and temporal temperature distribution of the target tissue,
      wherein the monitoring comprises acquiring magnetic resonance thermometry images of the target tissue, and
      wherein the magnetic resonance thermometry images of the target tissue provide the spatial and temporal temperature distribution of the target tissue;
   extracting thermal conductivity as a function of temperature for controlled increase of blood perfusion from a measured spatial and temporal temperature distribution of the target tissue during and after thermal stimulation;
   extracting a temperature dependent perfusion rate from the spatial and temporal temperature distribution of the target tissue during and after thermal stimulation, wherein the extraction of temperature dependent perfusion rate is based, at least in part, on the thermal conductivity;
   administering a therapeutic agent to the subject;
   providing a controlled thermal stimulation to the target tissue,
      wherein the controlled thermal stimulation is provided by the Magnetic Resonance guided high intensity focused ultrasound transducer while monitoring the spatial and temporal temperature distribution of the target tissue,
      wherein the controlled thermal stimulation results in a temperature dependent control of blood perfusion rate to the target tissue, thereby resulting in a temperature dependent controlled increase of blood perfusion to the target tissue, and
      wherein the controlled increase of blood perfusion results in accumulation of the therapeutic agent in the target tissue; and
   discontinuing delivery of ultrasound energy when the monitored temperature of the target tissue achieves a pre-determined set temperature or temperature profile.

9. The method of claim 8, wherein the therapeutic agent is activated by mechanical vibrations.

10. The method of claim 8, the controlled thermal stimulation is performed for a predetermined duration.

11. The method of claim 8, wherein the administration of the therapeutic agent occurs simultaneously with the controlled thermal stimulation of the target tissue.

* * * * *